(12) United States Patent
D'Andrea

(10) Patent No.: US 9,149,653 B2
(45) Date of Patent: Oct. 6, 2015

(54) BRACHYTHERAPY DEVICES AND METHODS FOR THERAPEUTIC RADIATION PROCEDURES

(71) Applicant: Mark A. D'Andrea, Houston, TX (US)

(72) Inventor: Mark A. D'Andrea, Houston, TX (US)

(*) Notice: Subject to any disclaimer, the term of this patent is extended or adjusted under 35 U.S.C. 154(b) by 295 days.

(21) Appl. No.: 13/786,640

(22) Filed: Mar. 6, 2013

(65) Prior Publication Data
US 2014/0257013 A1    Sep. 11, 2014

(51) Int. Cl.
*A61F 2/00* (2006.01)
*A61N 5/10* (2006.01)
*A61F 7/12* (2006.01)

(52) U.S. Cl.
CPC .......... *A61N 5/1002* (2013.01); *A61N 5/1048* (2013.01); *A61F 7/123* (2013.01); *A61F 2007/126* (2013.01); *A61N 2005/1003* (2013.01)

(58) Field of Classification Search
CPC ............... A61N 5/1002; A61N 7/123; A61N 2007/126; A61N 2005/1003; A61N 5/1048
See application file for complete search history.

(56) References Cited

U.S. PATENT DOCUMENTS

| | | |
|---|---|---|
| 3,060,924 A | 10/1962 | Rush |
| 3,861,380 A | 1/1975 | Chassagne et al. |
| 4,294,264 A | 10/1981 | Fischell et al. |
| 4,323,055 A | 4/1982 | Kubiatowicz |
| 4,434,789 A | 3/1984 | Kumar |
| 4,448,198 A | 5/1984 | Turner |
| 4,631,415 A | 12/1986 | Sauerwein et al. |
| 4,733,653 A | 3/1988 | Leung et al. |
| 4,798,215 A | 1/1989 | Turner |
| 4,861,520 A | 8/1989 | van't Hooft et al. |
| 4,881,937 A | 11/1989 | van't Hooft et al. |
| 4,881,938 A | 11/1989 | van't Hooft et al. |
| 4,897,076 A | 1/1990 | Puthawala et al. |
| 4,947,842 A | 8/1990 | Marchosky et al. |
| 4,967,765 A | 11/1990 | Turner et al. |
| 4,969,863 A | 11/1990 | van't Hooft et al. |
| 5,012,357 A | 4/1991 | Schoeppel et al. |
| 5,090,043 A | 2/1992 | Parker et al. |

(Continued)

FOREIGN PATENT DOCUMENTS

WO    WO 02/102451 A1    12/2002

OTHER PUBLICATIONS http://www.cancer.org/Treatment/TreatmentsandSideEffects/TreatmentTypes/hyperthermia. American Cancer Society. Mar. 3, 2011. Wayback machine internet archive.*

(Continued)

*Primary Examiner* — Christine H Matthews
*Assistant Examiner* — Joshua D Lannu
(74) *Attorney, Agent, or Firm* — Cook Alex Ltd.

(57) ABSTRACT

Radiation therapy or brachytherapy devices, systems and methods are in general catheter form and include at least one balloon that assists in placement of radio therapeutic members at desired treatment locations within an existing body cavity or at a site that was formed under a patient's skin for treatment purposes. One or more detectors, such as microdiodes, are present on the device, and a hyperthermia tube or the like is also included that delivers hyperthermia treatment for the target treatment site or sites. Data collected by the detector allows the medical professional to monitor radiation treatment and, when desired, interaction between hyperthermia treatment and radiation delivery by the radiation treatment member.

34 Claims, 12 Drawing Sheets

(56) References Cited

U.S. PATENT DOCUMENTS

| | | | |
|---|---|---|---|
| 5,106,360 | A | 4/1992 | Ishiwara et al. |
| 5,249,585 | A | 10/1993 | Turner et al. |
| 5,306,271 | A | 4/1994 | Zinreich et al. |
| 5,429,582 | A | 7/1995 | Williams |
| 5,520,646 | A | 5/1996 | D'Andrea |
| 5,653,683 | A * | 8/1997 | D'Andrea ............. 604/21 |
| 5,720,717 | A | 2/1998 | D'Andrea |
| 5,902,251 | A * | 5/1999 | vanHooydonk ......... 600/549 |
| 5,913,813 | A | 6/1999 | Williams et al. |
| 6,083,148 | A | 7/2000 | Williams |
| 6,312,375 | B1 | 11/2001 | Montebello et al. |
| 6,413,204 | B1 | 7/2002 | Winkler et al. |
| 6,482,142 | B1 | 11/2002 | Winkler et al. |
| 6,679,860 | B2 | 1/2004 | Stiger |
| 6,699,171 | B2 | 3/2004 | Harmon |
| 6,746,465 | B2 * | 6/2004 | Diederich et al. ......... 606/192 |
| 6,866,624 | B2 | 3/2005 | Chornenky et al. |
| 7,447,550 | B2 | 11/2008 | Eggers et al. |
| 7,476,235 | B2 | 1/2009 | Diederich et al. |
| 7,534,202 | B2 | 5/2009 | Eng |
| 7,556,596 | B2 | 7/2009 | Mourtada et al. |
| 7,651,458 | B2 | 1/2010 | Mourtada et al. |
| 7,666,130 | B2 | 2/2010 | Mick |
| 8,033,979 | B2 | 10/2011 | Mick |
| 8,423,152 | B2 | 4/2013 | Turner et al. |
| 2003/0153803 | A1 | 8/2003 | Harmon |
| 2005/0251235 | A1 | 11/2005 | Schlorff et al. |
| 2006/0030914 | A1 | 2/2006 | Eggers et al. |
| 2006/0116546 | A1 | 6/2006 | Eng |
| 2008/0086050 | A1 | 4/2008 | Misic et al. |
| 2008/0228063 | A1 | 9/2008 | Turner et al. |
| 2010/0100092 | A1 | 4/2010 | Turner et al. |
| 2010/0145132 | A1 | 6/2010 | Isham |
| 2011/0182880 | A1 | 7/2011 | Von Stein et al. |
| 2011/0200526 | A1 | 8/2011 | Parsai et al. |
| 2011/0224477 | A1 | 9/2011 | Issels |
| 2012/0215053 | A1 | 8/2012 | Gim |
| 2013/0177566 | A1 | 7/2013 | Ruben et al. |
| 2013/0261368 | A1 | 10/2013 | Schwartz |

OTHER PUBLICATIONS

BSD-500 Hyperthermia System brochure, BSD Medical Corporation, 2007.

BSD-2000 Hyperthermia System, BSD Medical Corporation 2010.

The International Search Report and the Written Opinion of the International Searching Authority, PCT/US2014/020507, dated Jun. 3, 2014.

Horton, John et al., LDR Intracavitary Brachytherapy Applicators, UT MD Anderson Cancer Center Intracavitary Brachytherapy, 2005.

http://www.cancer.org/Treatment/TreatmentsandSideEffects/TreatmentTypes/hyperthermia, Downloaded May 2, 2012.

Research Spotlight, Eos, vol. 92, No. 33, Aug. 16, 2011.

Zhu, Timothy C., Diode Dosimetry for Megavoltage Electron and Photon Beams, Dept. of Radiation Oncology, U. of Pennsylvania, Philadelphia, PA, Jun. 24, 2009.

Dutta, Pinaki, MD et al., How is radiation therapy given?, OncoLink Cancer Resources, www.oncolink.org/treatment/article, Downloaded Oct. 28, 2011.

http://vantageoncology.com/centers2006/html/body/treatment/wildomar, High-Dose Rate Brachytherapy (HDR)TandemandOvoid Implant, WildomarRadiationTherapyCentr, DownloadOct. 31, 201.

www.americanbrachytherapy.org/aboutBrachytherapy,What is Brachytherapy?, American Brachytherapy Society, Downloaded Nov. 4, 2009.

Section III: Disease Sites, Chapter 22: Uterine Cervix, textbook pp. 657-659, circa 2001.

Corrao, Anita, MS, CMA, DABRE, A comparison of APBI brachytherapy techniques: MammoSite . . . , Lifespan, Providence, RI, 2010.

MicroSelectron—body site applicator solutions, Oncoselect by Nucletron, circa Mar. 2010.

\* cited by examiner

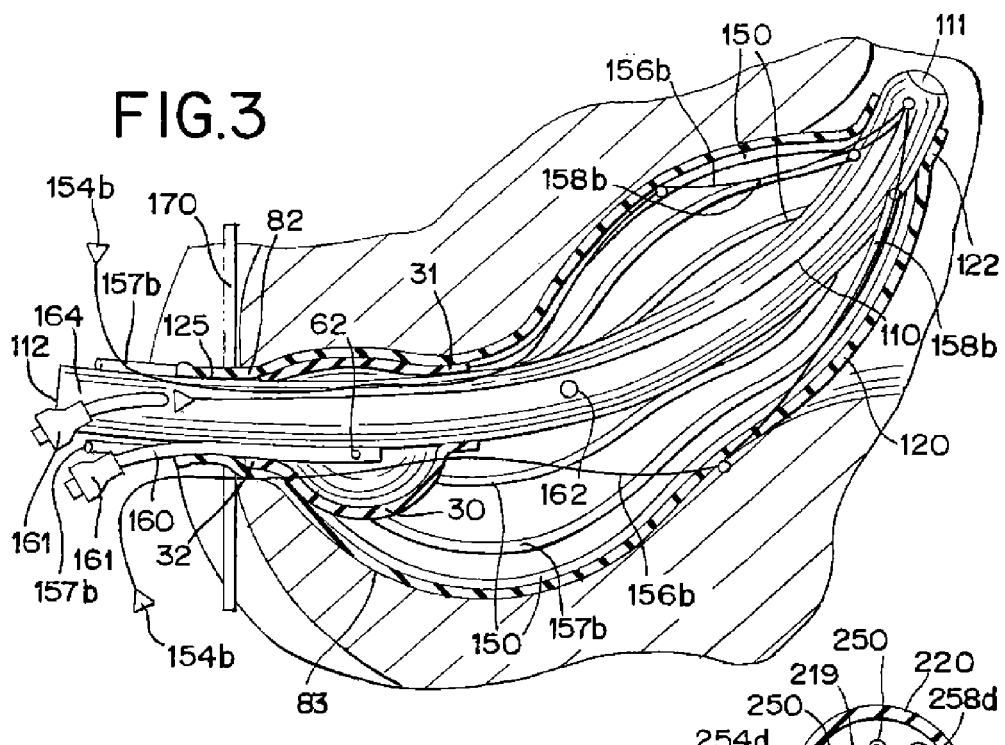
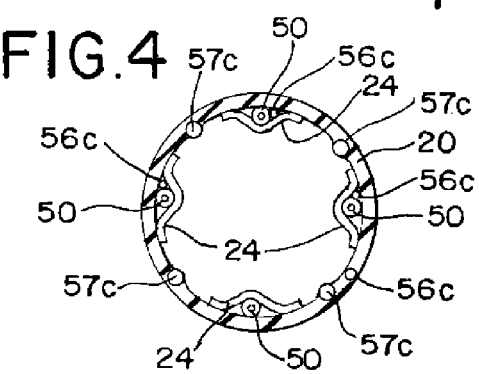
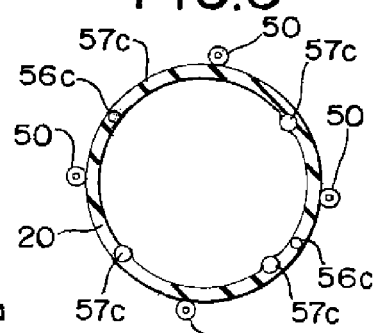
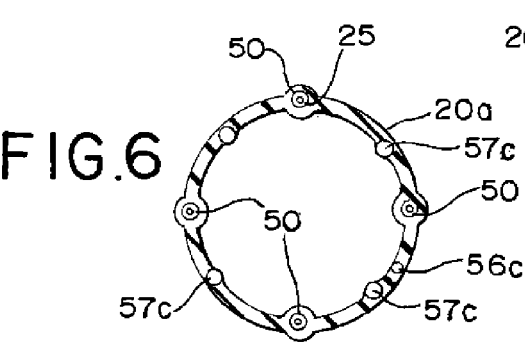

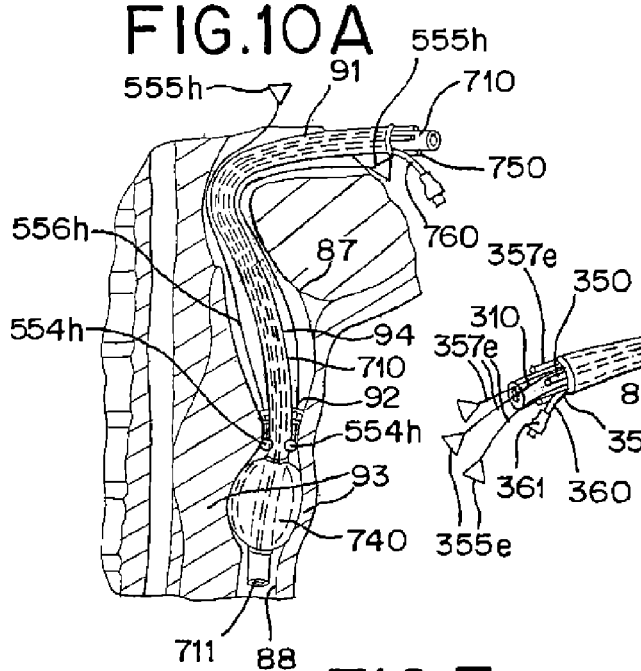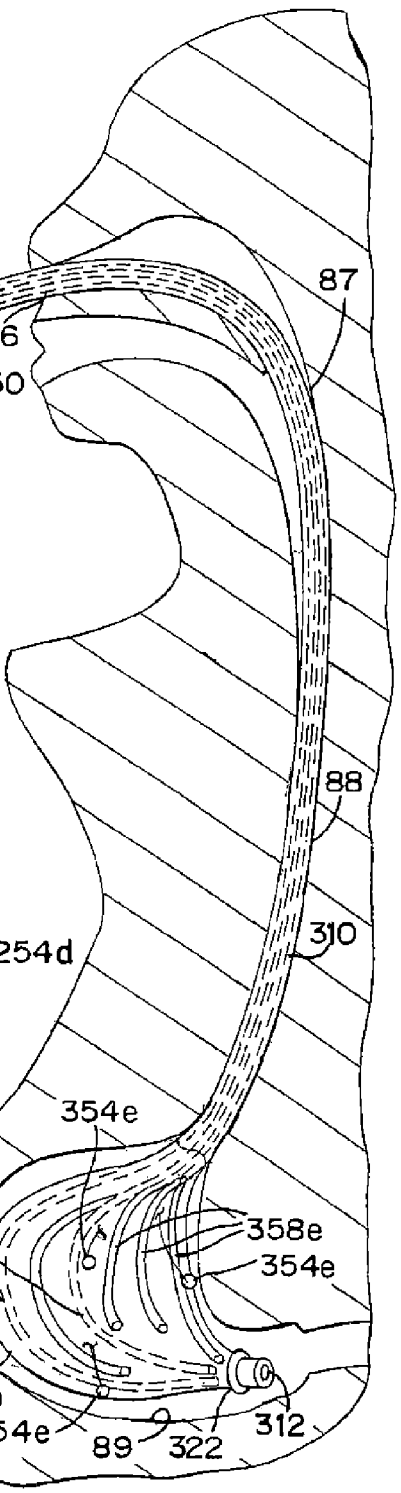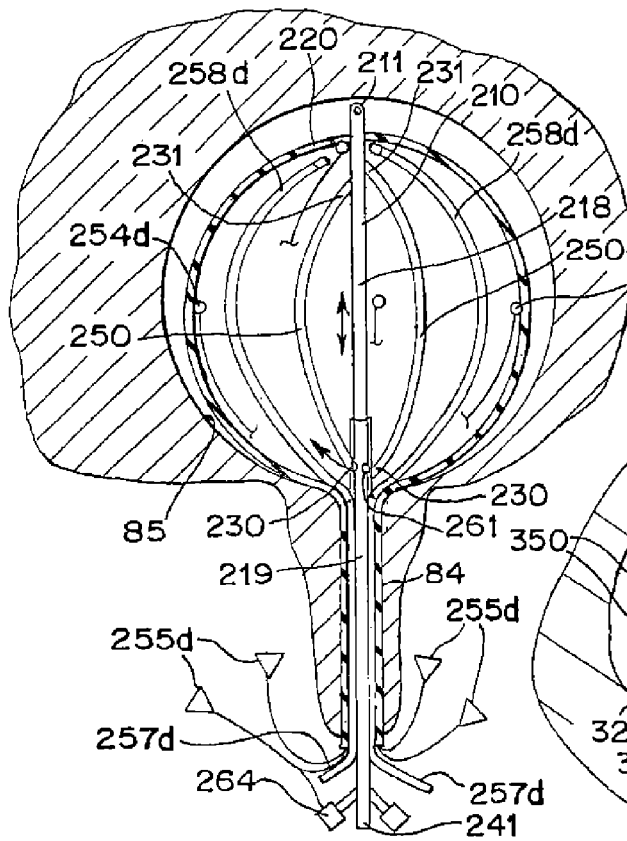

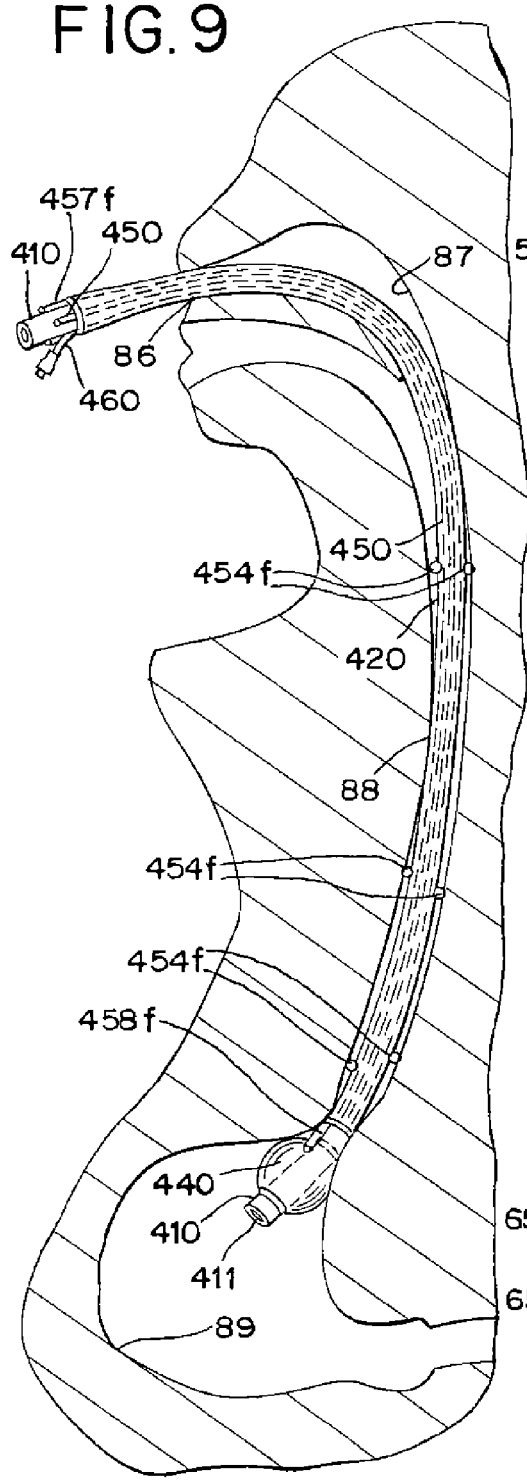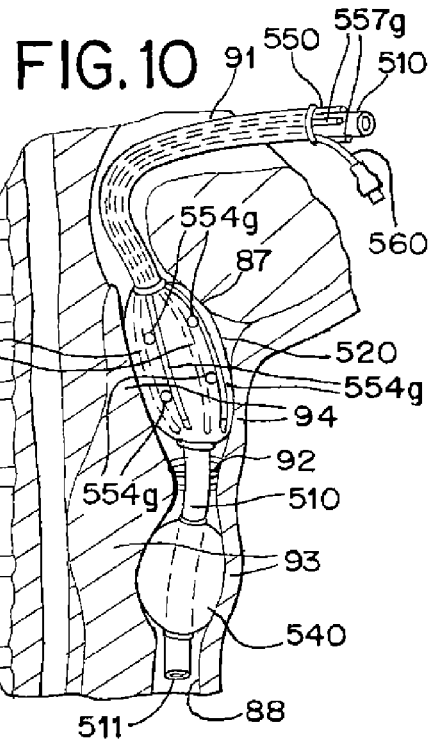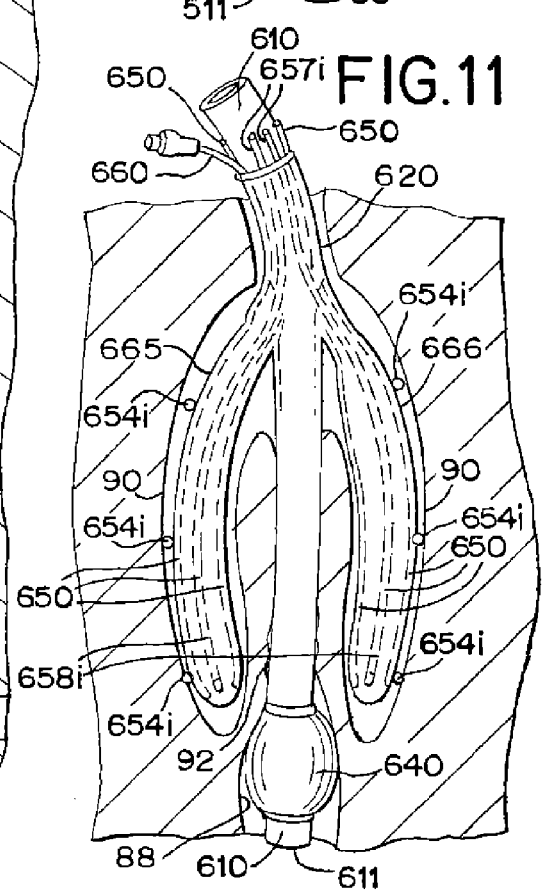

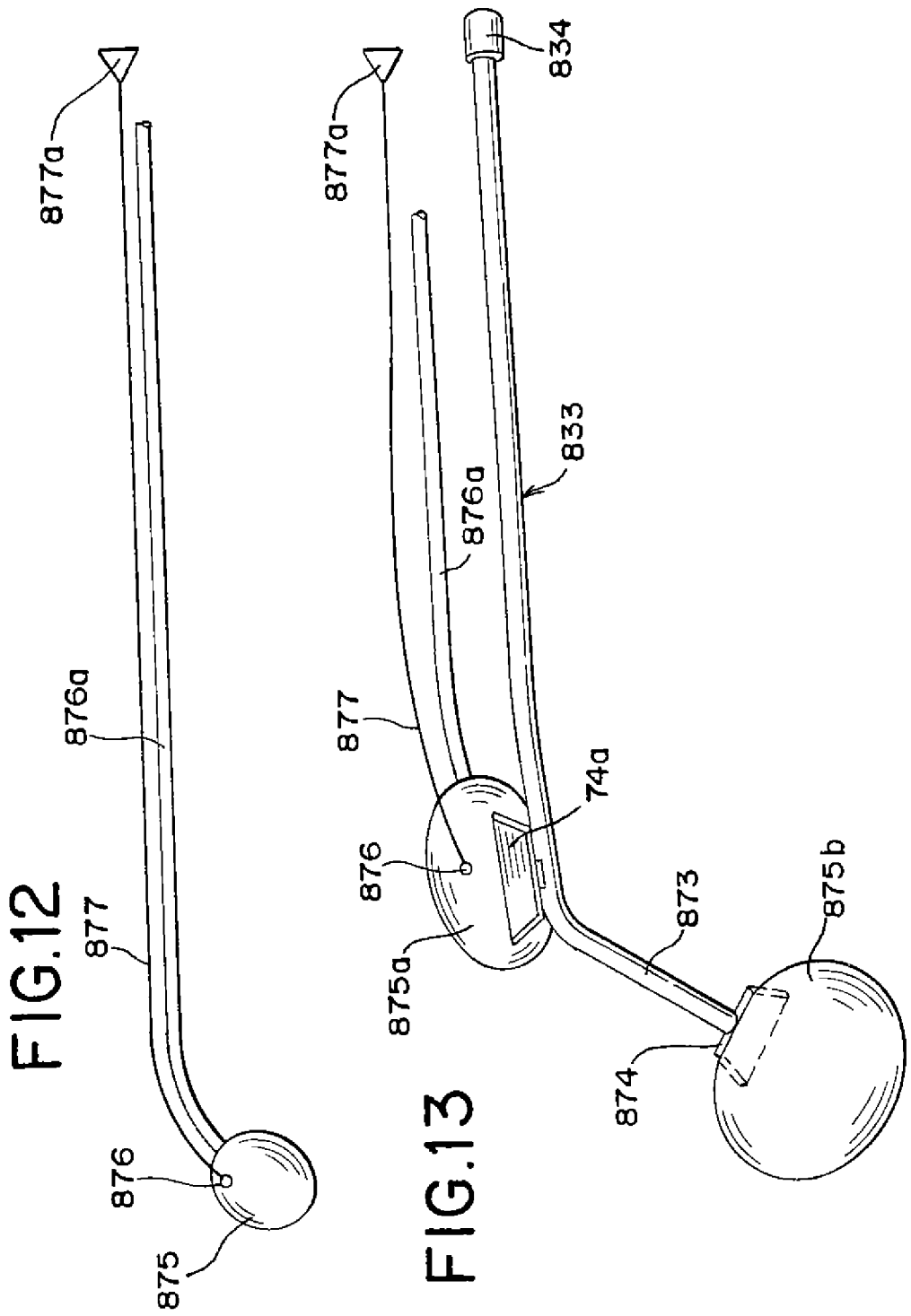

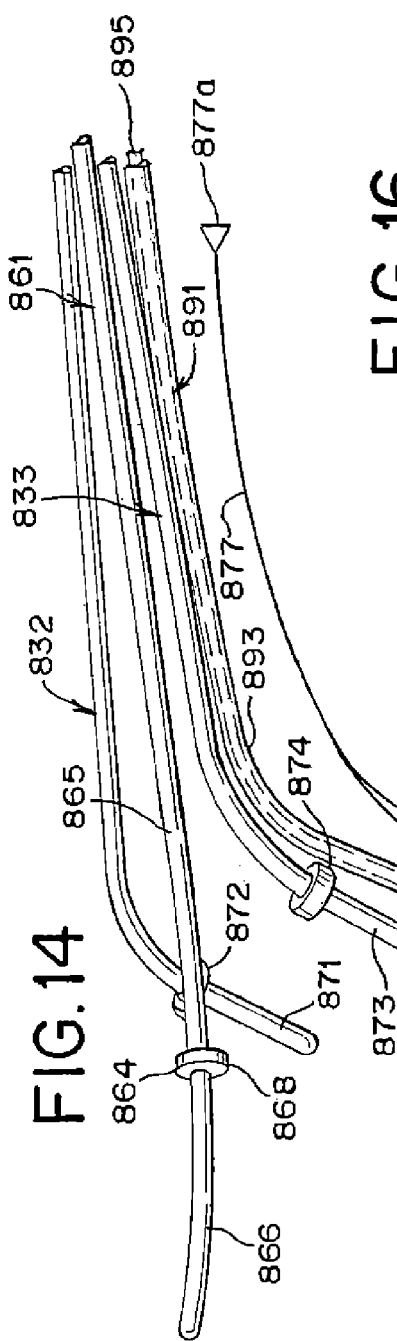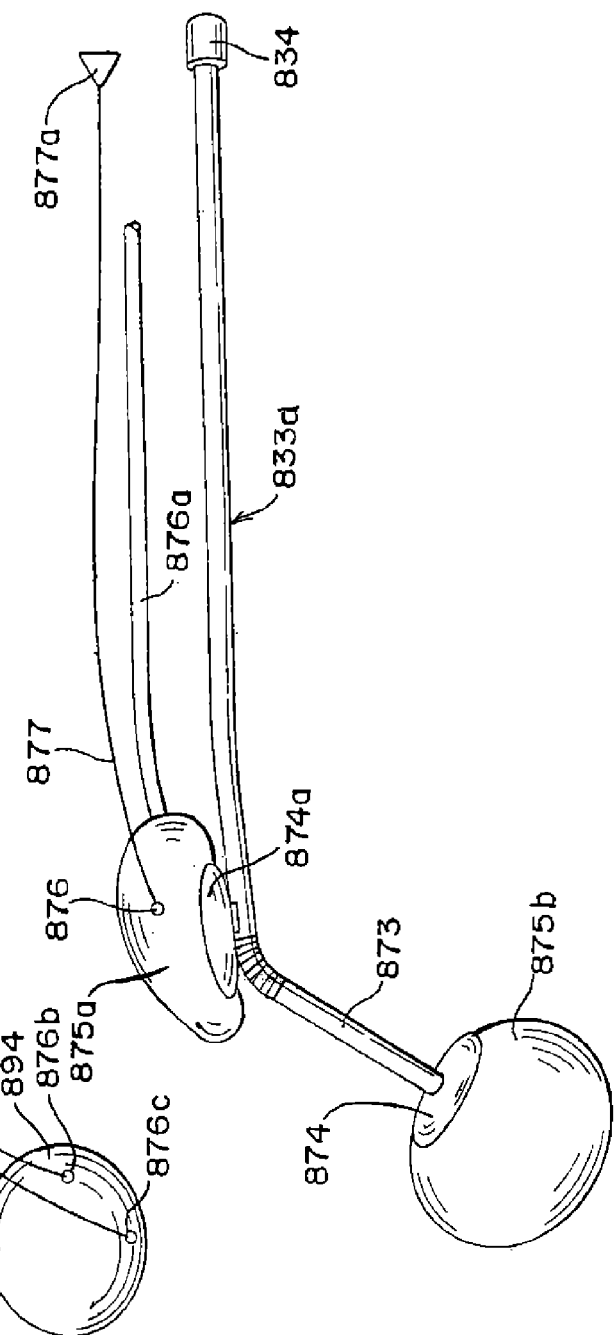

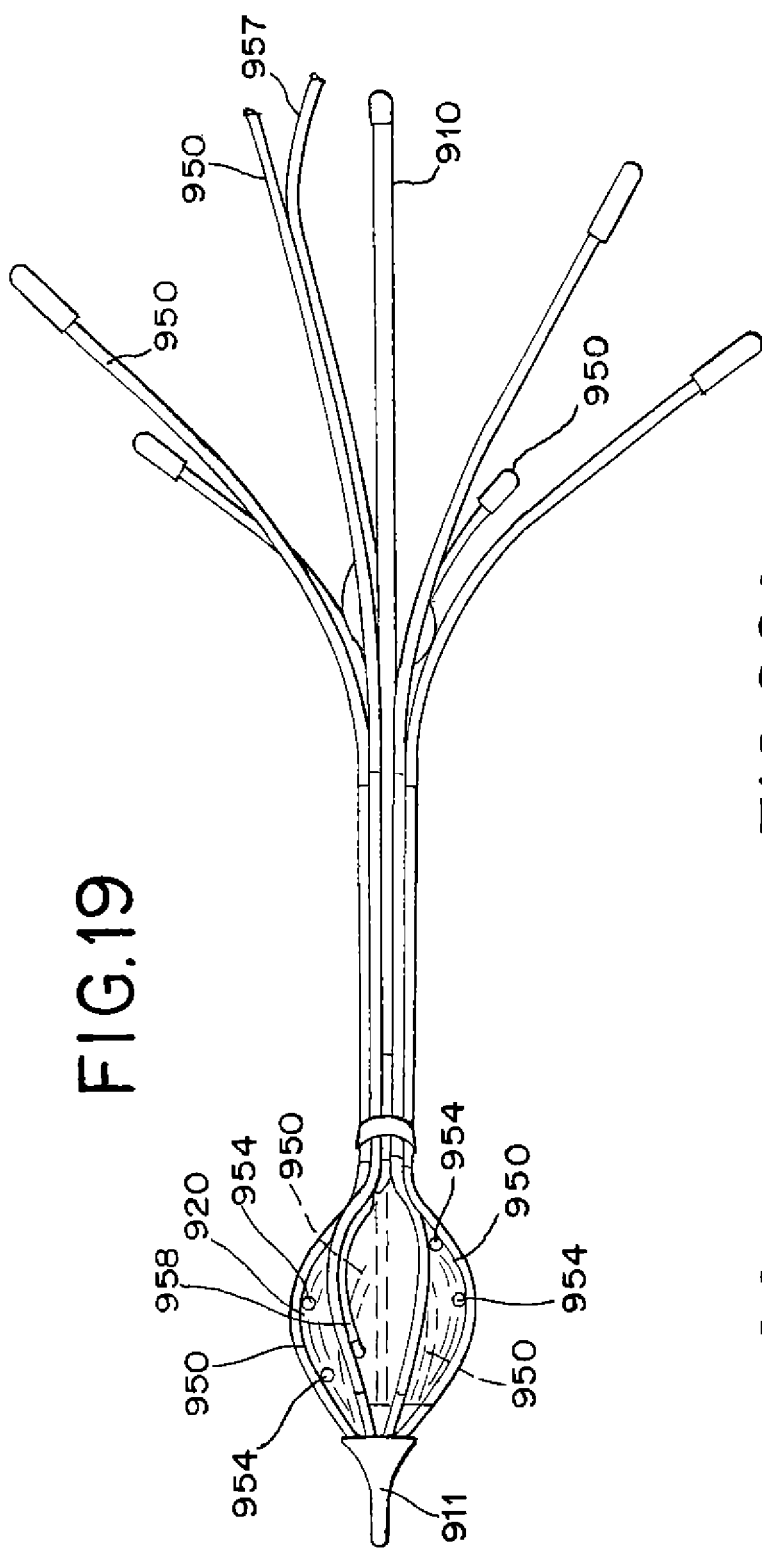

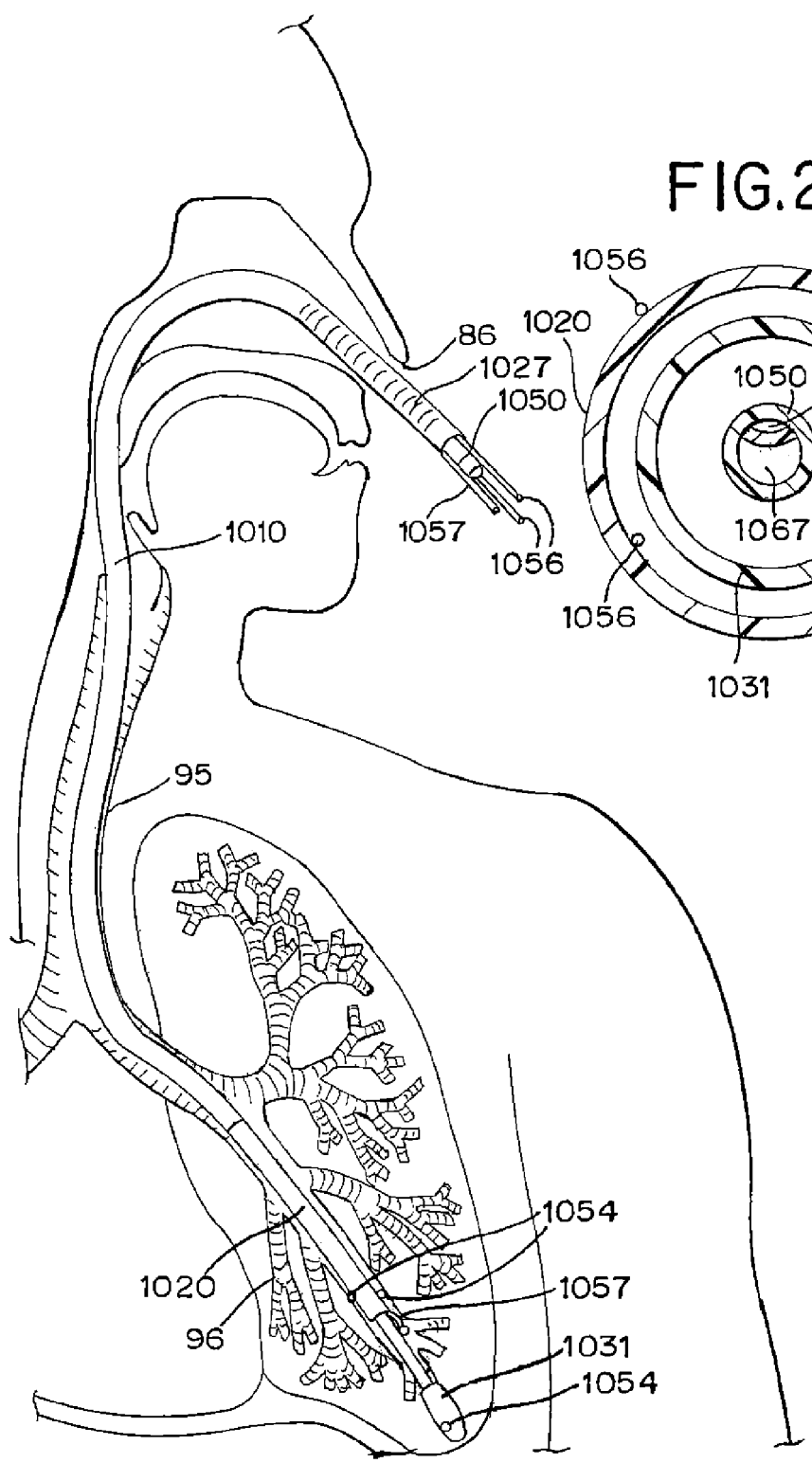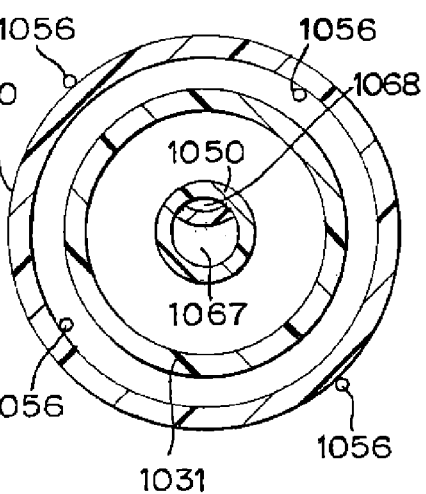
FIG. 23
FIG. 23A

BRACHYTHERAPY DEVICES AND METHODS FOR THERAPEUTIC RADIATION PROCEDURES

TECHNICAL FIELD

The present subject matter relates to systems, devices and therapeutic procedures used during radiation treatment. The field encompasses radiation oncology procedures with respect to a wide variety of cancerous conditions. Radioactive material is delivered by implements incorporating balloon technology in combination with other technologies which together enhance the precision and accuracy of brachytherapy treatment.

BACKGROUND

Numerous systems, devices and methods are known for brachytherapy use. Some of these incorporate balloons to achieve and maintain proper placement and/or as a component of radiation material delivery. Some incorporate multiple delivery paths for the radiation material.

Radiation oncology brachytherapy practitioners and researchers have developed various devices, systems and methods, each typically being designed for a specific diseased body organ or part and/or for one or more treatment regimens. Whether the treatment regimen is a one-step or multi-step protocol, it is important to maintain a good balance among radiation dosage, placement and timing. Timing can involve treatment and non-treatment intervals that vary depending upon the oncology protocol to be followed.

Carcinoma treatment procedures can follow a protocol calling for a series of multiple implants, such as when following high dose rate (HDR) brachytherapy. At times, the oncologist may choose to use a low dose rate (LDR) brachytherapy regimen, typically based on cesium delivery as $^{137}$Cs. For HDR brachytherapy regimens $^{192}$Ir is frequently used because of its high specific activity. Other isotopes are available and used as warranted. The degree of treatment is measured in terms of units of radiation exposure (in roentgens or Gray or Gy), and often these are prescribed at specific points. Details in this regard are known to radiation oncologists, medical physicists and other medical professionals experienced in brachytherapy. An objective often is to provide reasonably constant and predictable dose rates at each location at which the isotopes are applied.

Accordingly, it is clear that intracavitary radiation treatment and other brachytherapy that is not intracavitary, such as those gaining access through a surgical opening or access location, need to be exacting and specific in each of dose rates, durations and radiation target locations, for example. In addition, the closeness of tissues not intended to be irradiated should be taken into consideration. For example, in intrauterine treatment it is important to minimize, if not eliminate, radiation exposure to the bladder and rectum. Generally, brachytherapy devices are visible under X-ray images in order to ensure intended placement and to allow the medical physicist or professional to generate a radiation treatment plan specific for this placement and for the particular anatomy and disease location and severity for the particular patient and for this treatment event.

It will be appreciated that brachytherapy delivery systems can be used in treatments that are applied manually or remotely using remote afterloading systems. In remote afterloading systems, the radioactive materials are delivered from a safely contained source by way of hollow tubes to hollow treatment portions or locations. Radioactive material can be in the form of wires, seeds or other forms. In such systems, the radioactive material is typically delivered via remote control, such as by operation of a motor, after the medical professionals all are removed from the treatment room. Such remote delivery equipment can move the radioactive dose into the applicator already positioned within the body cavity.

SUMMARY

There are several aspects of the present subject matter that may be embodied separately or together in the systems, devices and methods described herein and claimed below. These aspects may be employed alone or in combination with other aspects of the subject matter described herein, and the description of these aspects together is not intended to preclude the use of these aspects separately or the claiming of such aspects separately or in different combinations as may be set forth in the claims appended hereto.

In one aspect, systems, devices and methods are provided for intracavitary brachytherapy with a catheter type component useful in connection with radiation therapy such as intracavitary oncology assemblies or systems for intracavitary radiation dose delivery.

In another aspect, the subject matter relates to therapeutic procedures, systems and devices used during radiation therapy and that incorporate a therapeutic balloon positioned along at least a portion of the length of the device. Radio therapeutic members, tubes or elongated rods for containing radioactive material are engaged by and move with the therapeutic balloon when it is expanded. These rods or the like may be inserted in elongated pockets of the therapeutic balloon; they may also be secured to the balloon with loops attached to the inner or outer surfaces of the balloon, or they may be secured to a balloon surface with adhesive strips, or they may be free-floating inside a balloon member. Catheter-type channels can be used for delivery of radioactive solutions, such as to the balloon, microdiodes can be incorporated to achieve real-time treatment capabilities, and hyperthermia components can be included.

In another aspect, the catheter and therapeutic balloon assembly is intended to be inserted into living body cavities such as through existing body orifices. Once the catheter and its therapeutic balloon are inserted in the prescribed manner into the body cavity, the balloon is inflated to move and hold the radioactive material into desired radiation treatment position within the body cavity during radiation therapy. The inflated therapeutic balloon also may be used to move, push, reposition, hold or otherwise manipulate body tissue during the radiation therapy. Radioactive solutions can be provided in the balloon, and microdiodes and hyperthermia channels can be incorporated.

In yet a further aspect, the physician is provided with equipment and techniques for treating any of a wide variety of cancers such as those inside or in the proximity of body cavities including the bladder, vagina, rectum, subglottic region, stomach, bronchial tubes, nasopharynx region, eye sockets, and other intracavitary areas. Interstitial insertion of the devices through tissue also are encompassed, such as in treatments of the breast, central nervous system, prostate, lung lesions and liver lesions. In these instances, insertion can be through a surgically made opening. Treatment can continue while the device is within the body and later retrieved or removed, typically depending on the treatment protocol being followed. Catheter-type channels can be used for delivery of radioactive solutions, such as to the balloon, microdiodes can be incorporated to achieve real-time treatment capabilities, and hyperthermia components can be included.

In a further aspect, a brachytherapy system and method includes at least one intracavitary balloon component that is sized, shaped, positioned and adapted to impart a space separation between the radiation source emanating from the device and an internal location within the body at which radiation treatment is not desired. Each balloon can be a separate unit provided in association with or secured to the device. In other approaches, one or more balloons are secured to a component of the device. Radiation treatment proceeds until a desired dosage is delivered, followed by removing the device or catheter component from the patient. Catheter-type channels can be used for delivery of radioactive solutions, such as to the balloon, microdiodes can be incorporated to achieve real-time treatment capabilities, and hyperthermia components can be included.

Another aspect facilitates long-term, low dose rate radiation by enabling introduction of nutrients or air or evacuation of wastes and/or gasses through a therapeutic treatment device itself. Catheter-type channels can be used for delivery of radioactive solutions, such as to the balloon, microdiodes can be incorporated to achieve real-time treatment capabilities, and hyperthermia components can be included.

Another aspect provides a system, device and method suitable for use in the bladder by providing an elongated insertion catheter having drainage characteristics. Catheter-type channels can be used for delivery of radioactive solutions, such as to the balloon, microdiodes can be incorporated to achieve real-time treatment capabilities, and hyperthermia components can be included.

Another aspect permits the physician to tailor the size of a radiation treatment device to the particular therapeutic requirements of the body cavity being treated. Catheter-type channels can be used for delivery of radioactive solutions, such as to the balloon, microdiodes can be incorporated to achieve real-time treatment capabilities, and hyperthermia components can be included.

Another aspect maintains the position of a therapeutic device through the use of a smaller, secondary balloon located within a larger, therapeutic balloon. Catheter-type channels can be used for delivery of radioactive solutions, such as to the balloon, microdiodes can be incorporated to achieve real-time treatment capabilities, and hyperthermia components can be included.

Another aspect provides a system, device and method suitable for use in the rectum by providing a large diameter catheter having drainage characteristics for liquid and/or air or other gas release from the rectum or other body cavity or treatment location. Catheter-type channels can be used for delivery of radioactive solutions, such as to the balloon, microdiodes can be incorporated to achieve real-time treatment capabilities, and hyperthermia components can be included.

Another aspect provides a system, device and method suitable for use in the vagina or rectum by providing a template which provides securement. Catheter-type channels can be used for delivery of radioactive solutions, such as to the balloon, microdiodes can be incorporated to achieve real-time treatment capabilities, and hyperthermia components can be included.

Another aspect provides a system, device and method suitable for use in the stomach by providing a catheter having inflow and outflow characteristics. Catheter-type channels can be used for delivery of radioactive solutions, such as to the balloon, microdiodes can be incorporated to achieve real-time treatment capabilities, and hyperthermia components can be included.

Another aspect provides a system, device and method suitable for use in the glotttic, superglottic or subglottic region by providing a catheter having inflow and outflow characteristics. Catheter-type channels can be used for delivery of radioactive solutions, such as to the balloon, microdiodes can be incorporated to achieve real-time treatment capabilities, and hyperthermia components can be included.

Another aspect provides a system, device and method suitable for use in the nasopharynx region by providing a catheter having inhalation and exhalation characteristics. Catheter-type channels can be used for delivery of radioactive solutions, such as to the balloon, microdiodes can be incorporated to achieve real-time treatment capabilities, and hyperthermia components can be included.

In a further embodiment, a method and system for brachytherapy includes a component for shielding body portions not intended for radiation therapy. Shielding can be accomplished by one or more shield members and/or by one or more balloons. Shielding can achieve one or more functions, such as blocking or reducing radiation transmission through the shielding and/or spacing radiation sources away from undesired treatment locations and/or moving portions of the body cavity walls at locations where treatment is not desired away from radiation sources. Catheter-type channels can be used for delivery of radioactive solutions, such as to the balloon, microdiodes can be incorporated to achieve real-time treatment capabilities, and hyperthermia components can be included.

An additional embodiment concerns a system and method for brachytherapy radiation therapy where a radiation detector and a radiation data receiver are included. In a particular embodiment, the radiation detector is positioned on or in a balloon component, which balloon component is sized, shaped and positioned to provide radiation therapy delivery, impart separation and/or positioning with respect to the radiation source of the colpostat.

A further embodiment concerns a system and method for brachytherapy radiation therapy which includes a hyperthermia sub-system having a thermal delivery location generally adjacent to a radiation delivery location of the system and method. In a particular embodiment, the hyperthermia sub-system is generally adjacent to a radiation delivery location of a balloon-containing device. In a further particular embodiment, the hyperthermia sub-system opens into the radiation delivery location of the catheter-like component.

Yet a further embodiment concerns a system and method for brachytherapy that includes, in combination, a hyperthermia sub-system and a radiation detector, both positioned in the close vicinity of the radiation delivery location along the catheter-like component. A radiation data receiver is located external of the body within which the brachytherapy is proceeding. Alternatively, the detector may be fixed and its data later able to be analyzed.

Another embodiment concerns a system and method for brachytherapy having a device featuring adjustability. With this embodiment, a portion of the device, such as a leg, is joined with the rest of the device such that the leg can be changed into its orientation. Same, in embodiments as desired, can be combined with balloon shielding, radiation detecting and/or hyperthermia features, systems and/or methods.

In a further embodiment, a method and system having a balloon and a catheter-like component further includes a component for shielding body portions not intended for radiation therapy. Shielding can be accomplished by one or more shield members and/or by one or more balloons. Shielding can achieve one or more functions, such as blocking or reducing radiation transmission through the shielding and/or spacing radiation sources away from undesired treatment locations and/or moving portions of the body cavity walls at locations where treatment is not desired away from radiation sources. In a further embodiment, the shielding function is combined with a shield and/or balloon along with adjustability to allow further tailoring of positioning of the shielding and/or balloon. Catheter-type channels can be used for delivery of radioactive solutions, such as to the balloon, microdiodes can be incorporated to achieve real-time treatment capabilities, and hyperthermia components can be included.

An additional embodiment concerns a system and method for brachytherapy radiation therapy where a radiation detector and a radiation data receiver are included. In a particular embodiment, the radiation detector is positioned on or in a balloon component, which balloon component is positioned on a colpostat that can feature adjustability to allow varied positioning of the radiation detector. Diodes or detectors may be fixed or may be able to be loaded into any length or position and be removed. Diodes in combinations herein are to be placed or spaced for evaluation of dose and radiation.

A further embodiment concerns a system and method with a balloon-containing device for brachytherapy radiation therapy which includes a hyperthermia sub-system having a thermal delivery location generally adjacent to a radiation delivery location of the system and method. In a particular embodiment the hypothermia delivery site is variable by being associated with an adjustable catheter component. In a further embodiment, the hyperthermia sub-system is generally adjacent to a radiation delivery location of an adjustable catheter component. In a further particular embodiment, the hyperthermia sub-system opens into the radiation delivery location of an adjustable catheter component.

Yet a further embodiment concerns a system, device and method for brachytherapy that includes, in combination, a hyperthermia sub-system and a radiation detector, both positioned in the close vicinity of the radiation delivery location of an adjustable catheter component. A radiation data receiver is located external of the body within which the brachytherapy is proceeding.

An additional further embodiment concerns a system, device and method for treatment of carcinoma within lung bronchus through the use of an elongated catheter having a balloon sleeve that longitudinally extends along a distal portion of the catheter, which balloon sleeve includes detectors, in combination with a secondary balloon that ensures secure placement of the elongated treatment balloon within the lung bronchus. In a particular embodiment, the elongated catheter has along its proximal portion a plurality of scale markings allowing the medical professional to reproduce placement of the treatment balloon and/or secondary balloon within the bronchus. A further embodiment includes hyperthermia treatment action. Another embodiment adds to a treatment catheter having a radiotherapy balloon associated with chemotherapy or analgesic delivery by being impregnated into, infused within, coated onto, or otherwise carried for delivery in combination with radiotherapy action.

BRIEF DESCRIPTION OF THE DRAWINGS

FIG. 3 is a generally schematic view that demonstrates an embodiment shown partially in cross section, in use within the rectum, shown in cross section;

FIG. 4 and FIG. 5 are cross-sectional views of the therapeutic balloon with radiation rods, demonstrating possible rod, microdiode and hyperthermia locations along the balloon contour;

FIG. 6 is a cross-sectional view showing the rod receiving members of the therapeutic balloon, demonstrating elongated pockets for therapeutic radiation rod insertion as well as microdiodes and hyperthermia tubes;

FIG. 7 is a generally schematic view that demonstrates another embodiment, shown partially in cross section, in use within the bladder, shown in cross section;

FIG. 7A is a cross section through the device embodiment illustrated in FIG. 7;

FIG. 8 is a generally schematic view that demonstrates another embodiment in use within the stomach, shown partially in cross section;

FIG. 9 is a generally schematic view that demonstrates another embodiment in use within the subglottic, superglottic or glottic region, shown partially in cross section;

FIG. 10 and FIG. 10A are generally schematic views that demonstrate other embodiments in use within the nasopharynx, hypopharynx, larynx and/or subglottic region(s), shown partially in cross section;

FIG. 11 is a generally schematic view that demonstrates another embodiment in use with the pyriform fossa, shown partially in cross section;

FIG. 12 is a detailed view of an embodiment of the distal portion of a colpostat of a brachytherapy system, including shielding and a "real time" dosing monitor arrangement;

FIG. 13 is a detailed view of an embodiment of the distal portion of an ovoid of a brachytherapy system, also including shielding and "real time" dosing monitoring;

FIG. 14 is a perspective view of a brachytherapy system including a balloon component and dosing monitoring with diode-type arrangement;

FIG. 16 is a detailed view of another embodiment of the distal portion of an ovoid of a brachytherapy system, having shielding, electronic dose monitoring and ovoid adjustability;

FIG. 17 is a perspective view of a brachytherapy system including a plurality of balloon components and dosing monitoring;

FIG. 18 is a perspective view of another embodiment of a brachytherapy system including a balloon component and monitoring arrangement;

FIG. 19 is a perspective view of a brachytherapy device suitable for interstitial insertion through tissue and radiation treatment at an internal location under the skin and tissue of the patient;

FIG. 20 is a cross-section through an embodiment of a balloon especially useful for treating areas of the body that are relatively elongated such as a prostate;

FIG. 20A is a cross-section through an embodiment of a balloon especially useful in treatment for situations where a flattened portion of a balloon will provide enhanced area for treatment or for supporting and/or protecting body portions that are not targeted for radiation treatment;

FIG. 22A is a cross-sectional view through the treatment balloon of FIG. 22;

FIG. 23 is a generally schematic view demonstrating another embodiment especially suitable for use in the long sac; and FIG. 23A is a cross-sectional view through the treatment balloon of FIG. 23.

DESCRIPTION OF THE ILLUSTRATED EMBODIMENTS

Figure 1:
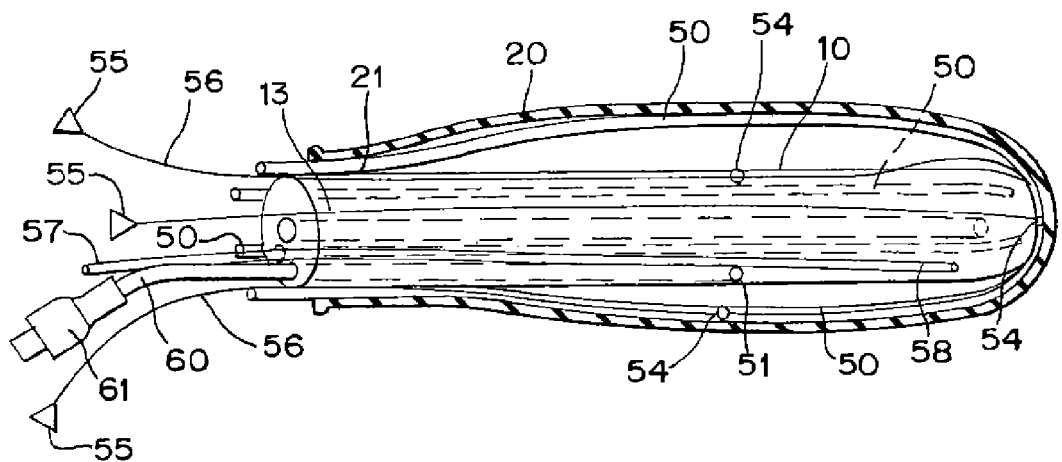
FIG. 1 is an elevation view of an embodiment including the therapeutic balloon in cross-section sealed to the catheter, inflation tube, and also radiation rods for following the contour of the balloon as well as diode and hyperthermia members.

The embodiments disclosed herein are exemplary only, and the subject matter described herein may be embodied in various forms. Therefore, specific details described herein are not to be interpreted as limiting the subject matter as defined in the accompanying claims.

Certain of the illustrated embodiments utilize a catheter for insertion into a body cavity. A therapeutic balloon is secured to a tubular catheter body, the balloon being positioned and sized for insertion into a particular type of body cavity to be treated. The proximal end of the catheter has one or a plurality of passageways to enable fluid communication through various channels in the catheter body, depending upon the embodiment. The passageways preferably utilize one- or two-way valves, regulators, hypodermic syringes, or the like for introduction, control, and/or withdrawal of fluids into and out of one or more balloons and/or body cavities.

The fluid with which the balloon found in certain embodiments may be filled can be a biocompatible gas, such as air, or a biocompatible liquid, such as saline solution. Balloons of various embodiments also can be inflated with, and contain, fluids that have a treatment function themselves. The balloon(s) of the catheter device may also be used to move, expand, or otherwise manipulate the body cavity by balloon inflation in order to provide more effective radiation treatment.

Radiation treatment members that can take the form of rods, tubes, fluids and/or solutions are associated with the therapeutic balloon so as to be properly positioned by or within the therapeutic balloon to effect the treatment, including intracavitary treatment. Such treatment can be by inflating the balloon to move treatment rods toward and/or in contact with the walls of the body cavity and/or by inflating the therapeutic balloon with radioactive fluid or solution thereby moving the fluid or solution closer to the target therapeutic treatment site. For example, the therapeutic balloon can contain rod receiving members which are used to hold the radiation treatment rods. The rod receiving members may be elongated pockets within the balloon material or strips of elastomeric or adhesive material along the circumference of the balloon and into which the treatment rods are inserted.

Alternatively, the treatment members (such as rods) are free-floating. Examples include providing multiple elongated treatment members inside of a balloon and that are secured at one or both of their end portions generally following end portions of the balloon. In such approaches, the elongated treatment members are able to bow out when within the balloon as it is inflated or expanded. Or the elongated treatment members may be positioned immediately inside the neck of the balloon where attached to the catheter and are otherwise freely suspended within the balloon, not necessarily secured to the balloon at distal portions. Even in that event, the elongated treatment members can be secured together at their respective distal end portions to facilitate bowing out of the elongated treatment members. Alternatively, the proximal portions of the elongated treatment members can be located within the polymeric material of the neck or between balloon material layers at the neck of the balloon to provide a gathering function for the portions of the elongated treatment members that fall in the area of the neck of the balloon.

Typical elongated treatment members are treatment rods contain small radioactive pellets or seeds which irradiate diseased tissue. In some embodiments, these rods have a lumen or lumens to accept the radioactive material, whether solid, liquid or gaseous. The size, dose rate and spacing of these radioactive sources such as seeds or pellets are prescribed by the physician and assembled prior to and/or during the procedure in which the catheter device is ready for insertion through the body cavity orifice and into the body cavity.

Different embodiments can utilize one or more different approaches to secure the catheter device during radiation therapy. These include a secondary inner balloon, a secondary distal balloon, one or two secondary outer balloons and associated tether catheters, a template, and a catheter lead.

When provided, the secondary inner balloon which usually is substantially smaller than the therapeutic balloon assists in holding the catheter device in place within the body cavity at the orifice and typically is located generally within and at the proximal end portion of the therapeutic balloon. Upon inflation, the secondary balloon secures the catheter device within the body cavity by restricting movement of the device at the body orifice. A secondary distal balloon, if and when included, is located distal of the therapeutic balloon. When inflated, it anchors the catheter device at a location downstream of the therapeutic balloon.

Some embodiments lend themselves to include a template to secure the catheter device at a location external of the body, such as a body cavity orifice or in areas surrounding a surgical opening. Such a template may be secured by one or combinations of multiple approaches. The template can be sutured to tissue in the vicinity of the body insertion location. The template can be adhered to tissue in the vicinity of the body insertion location, such as with an adhesive or glue. The template can be secured by attaching secondary catheters which are secured in orifices near the body insertion location. Securement may also be provided by a distally extending catheter lead which anchors the catheter device by slipping the distal end lead through a narrow section of the body, such as at the cervix or duodenum when a body cavity is treated.

Embodiments can incorporate a Foley-type catheter for radiation therapy in the bladder. When provided, the Foley-type catheter enables the necessary drainage of liquids or gasses, including urine or other body fluids like during the therapeutic procedure without having to move or remove the catheter device.

One or more detectors, such as a diode or a microdiode, facilitate treatment and evaluation of the radiation therapy regimen, typically in association with a hyperthermia treatment. Each detector senses and if desired leads to recordal of dose amounts and an indication of location. Detectors can be imbedded in another component such as a balloon or a catheter, or be positioned on or in such component. In many regimens, it is advantageous to provide detectors in a symmetrical array, for example evenly spaced from each other or from a reference location. Detectors also can be movable and/or removable. Positioning can be anterior, posterior, right plane, left plane, for example.

FIG. 1 shows a therapeutic balloon and catheter assembly, including a body or tube member 10, a therapeutic balloon and catheter assembly, including a body or tube member 10, a therapeutic balloon 20, radio therapeutic members such as the illustrated rods 50, and an inflation tube 60. The therapeutic balloon 20 is positioned over a distal end length portion of the catheter body member or cylinder 10. This distal end length portion and its therapeutic balloon 20 can be inserted by the physician in an intracavitary manner through a naturally occurring body orifice of a patient and into a body cavity in order to carry out a therapeutic radiation procedure, or can be inserted into the body apart from a pre-existing body cavity.

The therapeutic balloon 20 is typically made of a polymer material, including latex, and body-compatible or medical grade polymers. Catheter or cylinder 10 is typically made of a polymeric material, a metallic material, or a combination of polymeric with metallic material, such as strands of metal imbedded in polymer in order to create the desired balance of flexibility and rigidity. In this particular embodiment, the catheter can be substantially rigid and is more in the nature of a plastic carrier.

Figure 2:
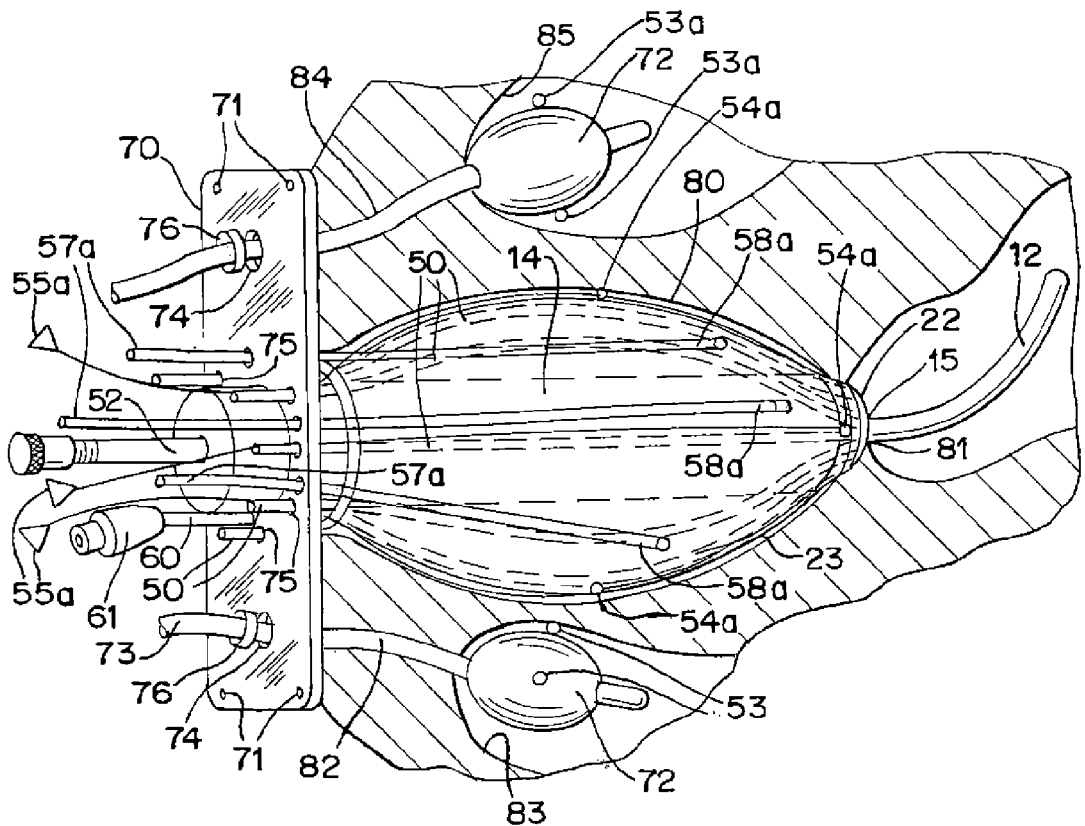
FIG. 2 is a perspective view that demonstrates an embodiment in use within the vagina, shown in cross section.

The therapeutic balloon may be shaped so as to be generally round, oblong, semicircular or curved along one side and flat along another side, such as being generally D-shaped in cross-section. The balloon in this embodiment is inflated by means of the inflation tube 60 which opens into the balloon through an orifice 51 to inflate and deflate the balloon as desired. Inflation tube 60 may be inserted between the catheter and therapeutic balloon as illustrated in FIG. 2, or as shown in FIG. 1, it may be within the catheter or plastic carrier 10 and pass through its wall and into the balloon at orifice 51. A proximal portion 21 of the annular inside surface of the balloon 20 is sealed about catheter or cylinder 14 at a distal annular portion 13. When an inflation tube exterior of the catheter is utilized, the seal must accommodate the profile of the tube. Fitting 61 connects with a pressurized fluid source and may include a valve or regulator. The pressurized fluid may be a biocompatible gas such as air or a biocompatible fluid such as saline solution. The means of pressurization may be a pressurized tank, an in-house line plumbed to the treatment room, a hypodermic syringe, or the like.

Typically, the radio therapeutic rods 50 are rendered radio therapeutic by being loaded with radioactive pellets, rice, seeds, wires or the like, as prescribed by the physician, either before or after insertion of the device into the body. Any other suitable member for effecting radiotherapy may be used provided it can be moved into position by the therapeutic balloon. Positioning of the rods may be aided by rod receiving members of the therapeutic balloon skin, described in more detail in connection with FIGS. 4 through 6. The device may be inserted into the living body for the therapeutic radiation procedure either prior to or following insertion of the radio therapeutic rods into the rod receiving members. Once the assembly and radio therapeutic rods are inserted into the cavity and secured, the balloon 20 is inflated to move the rods to the body cavity or treatment site, and radiation therapy of the diseased tissues is initiated and will continue for the prescribed duration, after which the balloon is deflated and the device removed.

A plurality of detectors 54 are positioned in general association with the radio therapeutic rods 50. Detectors in this regard are diodes, microdiodes, mini dosimeters or other data collecting devices that can be used to transmit data for "real time" measurement, observation and/or recordal of such data. For example, radiation data are collected in order to quantify radiation at a specific location along the device. In this regard, a data receptor 55 is provided. When desired, individual detectors 54 can have their own respective data receptors. Communication between the detectors 54 and data receptors 55 can be wireless or can enlist the use of a transmission wire or lead 56. FIG. 1 also incorporates a hyperthermia system by which heat can be applied to the cancerous area simultaneously with the radiation treatment, or if desired, in close association in time and location with the radiation treatment imparted with the radiation treatment indicated at detector 54. The illustrated hypothermia system includes a delivery tube 57 having a distal end portion 58. In this embodiment, the hyperthermia tube is shown at least partially within the tube member 10. When desired, the tubes can be used for low dose (LDR) or high dose (HDR) brachytherapy, e.g. microwave, ultrasound, radiant energy, or other type of method. Wires can be placed in the tubes for delivery with or without radiation, whether simultaneously, pre-irradiation, or post-irradiation.

FIG. 2 shows a modified form of the device of FIG. 1 in use in the vagina 80. This device further includes a template 70 and a distal end catheter tandem lead 12. The radio therapeutic rods 50 are loaded with radioactive pellets and slipped through openings 75 in the template 70 into the rod receiving members of the therapeutic balloon 23. The device may be inserted through the vaginal opening into the vagina 80 for the treatment procedure either prior to or following insertion of the radio therapeutic rods into the rod receiving members.

In this embodiment, the catheter is a substantially rigid cylinder 14 terminating in a substantially rigid, hemispherical section or dome 15. When provided, the catheter rigid tandem lead 12 protrudes from the dome, in which event, the balloon will not have a closed distal end as generally shown in FIG. 1, but it will have an annular connection leg 22 by which it is sealed to the cylinder end of the catheter. The rigid cylinder may have a polymeric surface and may be hollow or have passageways for loading radioactive material thereinto. When in use, the template 70 is located just outside of the body orifice and is used to hold the treatment device in position during the therapy. The template 70 is made of a polymeric or metallic material chosen for its rigidity and bored with several holes for allowing passage therethrough of the catheter and balloon assembly, radiation rods, blind end needles, and/or selected securement arrangements.

The template may be sutured or otherwise attached as discussed herein to nearby tissue. Typically, when suturing is followed same is through holes 71. When desired, the template 70 may also be secured with anchoring balloons 72 located in the bladder 85 and/or rectum 83. Anchoring balloons 72, when provided as illustrated in this embodiment, are located on tether catheters 73 which guide the balloons through the urethra 84 into the bladder 85 and through the anus 82 into the rectum 83, respectively, these tether catheters permitting inflation of the anchoring balloon(s) by means of passageways extending longitudinally through the catheter to a port located between the proximal and distal ends of the anchoring balloon. Fittings (not shown) are attached to the proximal ends of the catheters 73 for connection with pressurized fluid sources. The pressurized fluid may be a biocompatible gas such as air or a biocompatible fluid such as saline solution. When the balloons 72 are inflated and the tether catheters 73 are secured to the template 70 at holes 74, such as with clamps 76, the device is secured in the vagina 80 for treatment without requiring suturing.

Securement also may be achieved with rigid tandem or catheter lead 12 which is intended to be inserted through the cervix 81 of the patient. The tandem or catheter lead 12 is affixed to the distal end of the catheter or cylinder 14 and may be made of a metallic or polymeric material. The tandem or catheter lead 12 may itself accommodate radio therapeutic member(s), rod(s) and/or pellets for prescribed radiation therapy. Additional radio therapeutic members may be loaded into internal catheter capsule 52 which can extend beyond the proximal end of the catheter or cylinder 14 as shown.

With further reference to the embodiment depicted in FIG. 2, detector and hyperthermia components are illustrated. A plurality of detectors 54a are shown on the therapeutic balloon 23, data detectors 55a being included in this particular system. The illustrated hyperthermia system includes multiple delivery tubes 57a, each passing through the template 70, with their respective distal portions 58a being located in areas able to interact with the radiation delivery and detection locations.

Secondary balloons 72 may be attached or associated with the catheter device without the intermediate template 70, such as being directly attached to the catheter lead 12, cylinder 14 or catheter capsule 52. In line with other embodiments, either or both of these balloons 72 can include one or more detectors. For example, detectors 53 are provided on the balloon 72 within the rectum 83, and detectors 53a are provided on the balloon 72 within the bladder 85. These illustrated detectors are of the wireless variety, and they provide valuable treatment information or feedback to check on what, if any, dosage is reaching or had reached the rectum or bladder, which in the illustrated embodiment are not the target of radiation therapy.

FIG. 3 shows an embodiment for use in the rectum, including a catheter 110 which usually will be more flexible than the cylinder 14 of FIG. 2. A secondary balloon 30 is positioned within the therapeutic balloon 120 having radiotherapy members such as illustrated rods 150 and inflation tubes. The secondary balloon 30 can be omitted in some embodiments. A template 170 can also be included. The device is inserted through the anus 82 into the rectum 83.

The secondary balloon 30 that is illustrated in FIG. 3 is located within the therapeutic balloon 120, being sealingly affixed at its distal portion such as by leg 31. Balloons 30 and 120 may be inflated with the same inflation tube, or tube 160 for the secondary balloon 30 isolated from tube 164 for the therapeutic balloon 120 may be provided as shown. If two inflation tubes are used, each communicates through its length to a distal portion, respectively 62, 162, each port permitting inflation and deflation of each balloon. If the same inflation tube inflates both balloons, the therapeutic balloon and secondary smaller balloon are inflated by means of an inflation tube which has two isolated channels for fluid communication to the therapeutic and secondary balloons through separate ports. Fitting 161 connects with pressurized fluid sources as required. The securement or secondary balloon 30 is inflated until adequate securement is provided. Typically thereafter the therapeutic balloon 120 is inflated until adequate securement is provided.

Typically thereafter the therapeutic balloon 120 is inflated to move the rods 150 generally radially in an outward direction in order to bring the therapeutic radiation treatment as close as possible to the diseased tissue. The rods 150 are designed to move outwardly with a bowing action. Each rod can be secured in the area of the distal end of the balloon and/or in the area of the proximal end of the balloon 120. The bowing action allows the rods to move outwardly, even when inside the balloon 120 as shown in this embodiment. They are somewhat like the spokes of an umbrella, and can be substantially uniformly spaced from each other and bow outwardly providing a more homogeneous dosage from the rods 150. In the embodiment illustrated in FIG. 3, the respective distal ends of the rods are not connected as such, allowing movement of the rods, which are not expandable, with respect to the expanding balloon, and thus facilitating bowing action.

When provided, a template 170 is located just outside of the anus 82 in this embodiment and is used to hold the device in position during the therapy. The template 170 is bored with several holes for the catheter and balloon treatment device, for extra radiation rods, for suturing, and the like. This template arrangement may be used alone or in combination with the securement balloon, or the securement balloon alone may be used.

The catheter 110 has an opening or hole 111 at its distal end which communicates longitudinally through the length of the catheter to an outlet 112 at the proximal end of the catheter, thereby permitting the flow of excrement, liquid or gas from the intestines during the procedure. The opening or hole 111, outlet 112 and the passageway with which they communicate are intended to be of cross-section sufficiently large to enable flow of excrement. The opening of the hole 111 preferably is rounded to facilitate insertion in a non-traumatic fashion. The distal end of balloon 120 is sealed near the distal end of catheter 110 such as at leg 122. Proximal end portion or leg 125 of the therapeutic balloon and, when provided, proximal leg 32 of secondary balloon 30 is sealed in pressure-resistant fashion to the catheter 110 by known procedures.

With further reference to the embodiment depicted in FIG. 3, detector and hyperthermia components are illustrated. A plurality of detectors 154b are shown on the therapeutic balloon 120, data receptors 155b and transmission wires 156b being included in this particular system. The illustrated hyperthermia system includes multiple delivery tubes 157b, each passing through the template 170, with their respective distal portions 158b being located in areas able to interact with the radiation delivery and detection locations.

FIGS. 4 through 6 show three manifestations of the manner by which the radiation rods can be associated with the large therapeutic balloon of the various embodiments so as to move with the balloon and generally follow its contour when it is inflated and deflated. Arrangements for receiving the radio therapeutic components may be provided, such as the elongated pockets 25 of the balloon 20a shown in FIG. 6. Rod receiving members may take the form of strips 24 about a portion or the entire circumference of the balloon, the strips being made of polymeric, elastomeric or adhesive material, or other arrangement such that the rod will follow the balloon movement. The objective of the radio therapeutic component receiving members is to first restrict and then to effect movement of the radio therapeutic components by positioning them by or onto the balloon during insertion through the orifice and into the body cavity in this embodiment and to bring the components or rods as near as possible to the cavity tissue. FIG. 4 shows radio therapeutic rods located on the interior of the balloon. FIG. 5 shows radio therapeutic rods located on the exterior of the balloon, which can avoid the need for any discrete receiving members because the rods will be pushed outwardly by the expanding balloon. FIG. 6 shows radio therapeutic rods located within the balloon material itself. These designs provide radiation therapy along the contour of the balloon. Inflation of the balloon within and to the body cavity locates the radiation rods at the surface of the body cavity tissue.

In each of FIG. 4, FIG. 5 and FIG. 6, detector data transmission lines 56c are illustrated, either captured within a strip 24 or embedded within the wall of the therapeutic balloon 20, 20a. In addition, hyperthermia delivery tubes 57c are shown in association with the therapeutic balloon 23. In these embodiments, multiple delivery tubes 57c are shown embedded within the balloon wall. When desired, same could also be affixed to the balloon by straps or the like.

FIG. 7 shows an embodiment for use in the bladder and can be suitable for use elsewhere as well, including a catheter 210 and a therapeutic balloon 220 and inflation tube 264. Radio therapeutic rods 250 are secured to the catheter at a proximal end portion 230 of each and at a distal end portion 231 of each.

The radio therapeutic rods 250 are loaded or preloaded with radioactive pellets, rice, seeds, wires or the like as prescribed by the physician and then slipped into the rod receiving members of the therapeutic balloon. The assembly is inserted through the urethra 84 and into the bladder 85.

With further reference to the embodiment depicted in FIG. 7, detector and hyperthermia components are illustrated. A plurality of detectors 254d are shown on the therapeutic balloon 220, data detectors 255d being included in this particular system. Pluralities of hyperthermia tubes 257d with distal end portions 258d are illustrated at locations within the balloon in this particular embodiment. This embodiment also is illustrated in FIG. 7A. It will be noted the radio therapeutic rods 250 need not be evenly spaced from the balloon 220, from the detectors 254d and/or from the distal end portions 258d of the hyperthermia tubes 257d. This can be achieved by providing rods of differing lengths and/or by allowing independent relative movement of respective proximal end portions 230 and/or distal end portions 231 of the rods, such as by having separate sliding lengths of the proximal section 219 of the catheter 210 to which the independent respective proximal end portions 230 of the rods are attached, or by extending (either by added members or providing extra length to each independent rod) in the proximal direction. Whatever approach is used, typically the structure used to adjust the length of the rods 250, whether as a group or independently, is accessible outside of the body when the device is fully inserted.

The proximal end of the therapeutic balloon 220 is secured at a location on the catheter 210 as generally illustrated in FIG. 7. The illustrated catheter 210 is of a telescoping type such that a distal portion 218 thereof is slidably mounted within a proximal portion 219. Longitudinal movement of the distal and proximal portions of the catheter modifies the extent of bowing developed in each radio therapeutic rod 250. For example, moving the proximal portion 219 downwardly (as seen in FIG. 7) increases the distance between the proximal end portion 230 and the distal end portion 231 of the therapeutic rods 250, resulting in the radiation sources moving farther from the body tissue in order to (all other things being equal) decrease the radiation treatment provided by each therapeutic rod 250.

The therapeutic balloon 220 is inflated by means of the inflation tube 264. The therapeutic balloon 220 is inflated or deflated (or reduced in inflation) to bring the therapeutic radiation treatment as close as possible to the diseased tissue. This action also can be used to modify the location of the detectors 254d with respect to the radiation sources. Action of the balloon 220 or other member to which the detector is attached combined with action of the longitudinally adjustable catheter is available to adjust the spacing between the detector and the radiation source and/or between the radiation source and the tissue to be treated and/or between the detector and the tissue to be treated.

In this embodiment one may have the catheter 210 be of the Foley-type to enable urine, gas or other fluid flow out of the body during the therapy. The Foley-type catheter features a hole at the distal end 211 which communicates through a passageway within the catheter to a drain tube 241 located at the proximate portion of the catheter. FIG. 7 shows the male bladder, but the device is also usable in the female bladder. The presence of body fluid and/or gas during radiation treatment will distort body tissue, such as the rectum, and prevent its good separation from other tissue, such as prostate, and relieving the fluid and/or gas is a means for controlling undesired distortion during radiation treatment.

FIG. 8 shows an embodiment for use of the device in the stomach. This embodiment as illustrated includes an elongated catheter 310, catheter lead 312, therapeutic balloon 320, radio therapeutic rods 350, and an inflation tube 360. The radio therapeutic rods 350 are preloaded with radioactive pellets and then slipped into the channels of the therapeutic balloon. Catheter lead 312 guides the catheter into the mouth or the nose 86, through the nasopharynx region 87, through the subglottic region 88 and into the stomach 89. Once inserted into the prescribed location, the catheter lead 312 may be inserted into a narrow region of the stomach, such as the duodenum. The therapeutic balloon is inflated by means of the inflation tube 360. Inflation tube 360 may be inserted between the catheter 310 and the therapeutic balloon 320. Balloon 320 is sealed about catheter 310 over inflation tube 360 at leg portion 322. Fitting 361 is for connection to a pressurized fluid source in a manner generally discussed herein or as otherwise known.

With further reference to the embodiment depicted in FIG. 8, detector and hyperthermia components are illustrated. A plurality of detectors 354e are shown on the therapeutic balloon 320, data detectors 355e being included in this particular system. Also, a plurality of hyperthermal tubes 357e with distal end portions 358e are illustrated in this embodiment.

FIG. 9 shows an embodiment for use in the subglottic region. This embodiment of the invention includes an elongated catheter 410, a therapeutic balloon 420, radio therapeutic rods 450, and inflation tube 460. The radio therapeutic rods 450 are preloaded with radioactive pellets and then slipped into the rod receiving members of the therapeutic balloon. The assembly is inserted through the nose 86, through the nasopharynx region 87 and through the subglottic region 88 until the smaller secondary balloon 440 reaches the stomach 89.

The smaller secondary balloon 440, when provided, is located distally of the therapeutic balloon 420 at the distal end of the catheter 410 and is intended to provide securement to the device by anchoring it in the stomach 89. This secondary balloon 440 is similar in function to the secondary balloons 130 and 230 shown in FIG. 3 and FIG. 7, respectively, but this securement or secondary balloon 440 is located outside and distal of the therapeutic balloon.

The therapeutic balloon 420 and secondary smaller balloon 440 may be inflated, for example, by means of the inflation tube 460 which has two isolated channels for fluid communication to the therapeutic and secondary balloons. The secondary balloon 440 is inflated until adequate securement is provided and the therapeutic balloon 420 is inflated to bring the therapeutic radiation treatment as close as possible to the diseased tissue at the location of the subglottic region, for example. The catheter 410 has a hole 411 at its distal end which communicates longitudinally through the length of the catheter. The elongated longitudinal passageway which is thus provided is intended to permit the flow of nutrients and/or wastes during the radiation therapy procedure which can take several hours or even days.

Also illustrated in FIG. 9 is a plurality of detectors 454f positioned generally along the therapeutic balloon 420, generally in paired fashion. These are for passing data to a remote data receptor (not shown) by wireless means. A hyperthermia delivery tube 457f, having distal end portion 458f, is shown within the therapeutic balloon 420, leaving same at a cuff area in the vicinity of the secondary balloon 440.

FIGS. 10 and 10A illustrate embodiments for use in the nasopharynx, hypopharynx, subglottic and/or superglottic regions. This assembly of FIG. 10 includes the catheter 510, therapeutic balloon 520, secondary balloon 540 (when provided), radio therapeutic rods 550, and inflation tube 560. The radio therapeutic rods 550 are preloaded with radioactive pellets, rice or the like and then slipped into the rod receiving members of the therapeutic balloon 520. The assembly is inserted through the nose or mouth 91 and through the nasopharynx region 87 and past the vocal chords 92 until the smaller secondary balloon 540 reaches the subglottic region 93 proximate to the esophagus 88. At this stage, the secondary balloon 540 can be inflated to secure the device in place. Inflation of the therapeutic balloon 520 moves the radiotherapy materials outwardly to treat the superglottic region 94.

The therapeutic balloon and secondary smaller balloon are inflated by means of one or two inflation tubes 560. The secondary balloon 540 is inflated until adequate securement is provided by its engagement in the subglottic 88 or esophagus 93 areas and the therapeutic balloon 520 is inflated to bring the therapeutic radiation treatment as close as possible to the diseased tissue. The catheter 510 has a hole 511 at its distal end which communicates longitudinally through the length of the catheter to provide a longitudinal passageway for permitting inhalation and exhalation during the radiation therapy procedure. Each of FIG. 10 and FIG. 10A have detectors 554g, 554h, respectively. The embodiment of FIG. 10A shows transmission leads 556h and data receptors 555h, whereas FIG. 10 illustrates a wireless system. Hyperthermia conduits 557g are further illustrated.

In the FIG. 10A embodiment, the therapeutic balloon 740 is sized, shaped and positioned for treatment of the subglottic region 88 or esophagus 93. While a secondary or securement balloon could be included for engagement in the superglottic region 94, such is typically not required because the therapeutic balloon 740 often will adequately anchor the device. Treatment tubes 750 can extend through the tubular catheter body 710 as shown.

Alternatively, the therapeutic balloon 740 can be loaded with radio therapeutic materials prior to, during or after deployment of the device. This feature, which is also optional in any of the other embodiments, provides an especially uniform treatment dosage throughout the balloon when such uniformity is a desired feature of the treatment regimen. It can be particularly useful where the catheter is of considerable length or must bend significantly when in use, for example in the embodiments of FIG. 7 through FIG. 11. Balloon 740 inflation is through passageway 760, and fluids can pass through the catheter 710 between its proximal end and the distal opening 711.

An embodiment for use in the hypopharynx is illustrated in FIG. 11. This device includes a catheter 610, a secondary balloon 640 (when included), radio therapeutic tubes or rods 650, and an inflation tube 660. The therapeutic balloon 620 for this embodiment may be split at a generally proximal location into two chambers 665, 666 which inflate into each pyriform fossa. The radio therapeutic rods 650 typically are preloaded with radioactive members or materials and then positioned for movement with the balloon 620 such as by being slipped into rod receiving members of the therapeutic balloon. The therapeutic balloon is inserted into the hypopharynx 90. If needed the secondary balloon 640 can be inserted into the subglottic region. The therapeutic balloon 620 and secondary balloon 640 are inflated by means of one or two inflation tubes 660. A hole 611 and longitudinal passageway throughout the catheter 610 permit respiration during the course of the radiation therapy procedure. Multiple wireless detectors 654i are shown along the bifurcated therapeutic balloon 620, each also having positioned therewithin a hyperthermia delivery tube 657i having distal ends portions 658i.

Illustrated in FIG. 12 is a balloon arrangement that can be implemented for patient protective reasons. A balloon 875 is shown positioned over the end portion of a colpostat. This balloon typically can be useful in pushing away tissue, such as rectum tissue, for example, when it is inflated, only part inflation shown. It can also be a therapeutic balloon as generally discussed herein. Balloon inflation shown is carried out by passing saline solution or gas such as air or nitrogen through a catheter or conduit 876a to the balloon 875 from a source of inflation fluid (not shown). The balloon can exhibit one or more of the functions of balloons discussed herein.

In this embodiment, a detector 876 is on or associated with the balloon 875 in order to detect and measure in vivo dosing and radiation. If desired, "real time" detection, measurement, observation and/or recordal of radiation data can proceed. Typically the detector is placed in an area distal to a shield or in or on a balloon near such a location. Transmission of the detector data can be by a wireless system, or a transmission wire or lead 877 can be used, a data receptor 877a being shown. A typical detector is a microdiode.

FIG. 13 shows a colpostat having an elongated catheter body and a distal end portion treatment location, being an ovoid component, generally designated 833. This ovoid colpostat has an internal distal delivery location 873. This ovoid colpostat can include a shielding element 874 and a second shielding element 874a included in this embodiment, being positioned near the primary bend of this ovoid. A balloon 875a is shown in this same general location and has a detector 876 and catheter or conduit 76a similar to FIG. 12. Balloon 875b can be positioned for pushing away bladder tissue in this embodiment and can also include radio therapeutic receiving members (not shown) on, in or otherwise associated with the balloon which may include one or more detectors as generally discussed herein.

This balloon can exhibit one or more of the functions of balloons discussed herein. Shield 874a can be considered to sit on top of the colpostat to shield the bladder. Usually, these shielding elements 872, 874, 874a are medial and face each other when in use. Shielding material of the embodiments illustrated in FIG. 12 and FIG. 13 can be made of lead, tungsten, stainless steel, other metal, or a metal impregnated polymer, such as a lead-impregnated polymer.

The balloon of FIG. 14 or other embodiments may have radiopaque marking or may be radiopaque in whole or in part. Alternatively or additionally, the balloons of the various embodiments may include microdiodes attached or other devices or systems to provide "real-time" in vivo measuring of radiation. To this end one or more detectors are shown while transmission associated with same can be wireless connection lead or wire 877 is shown leading to data receptor 877a in FIG. 14. In FIG. 14, two detectors 876b and 876c are shown. These detect radiation at different locations and can have a common lead or separate leads to the data receptor.

Figure 15:
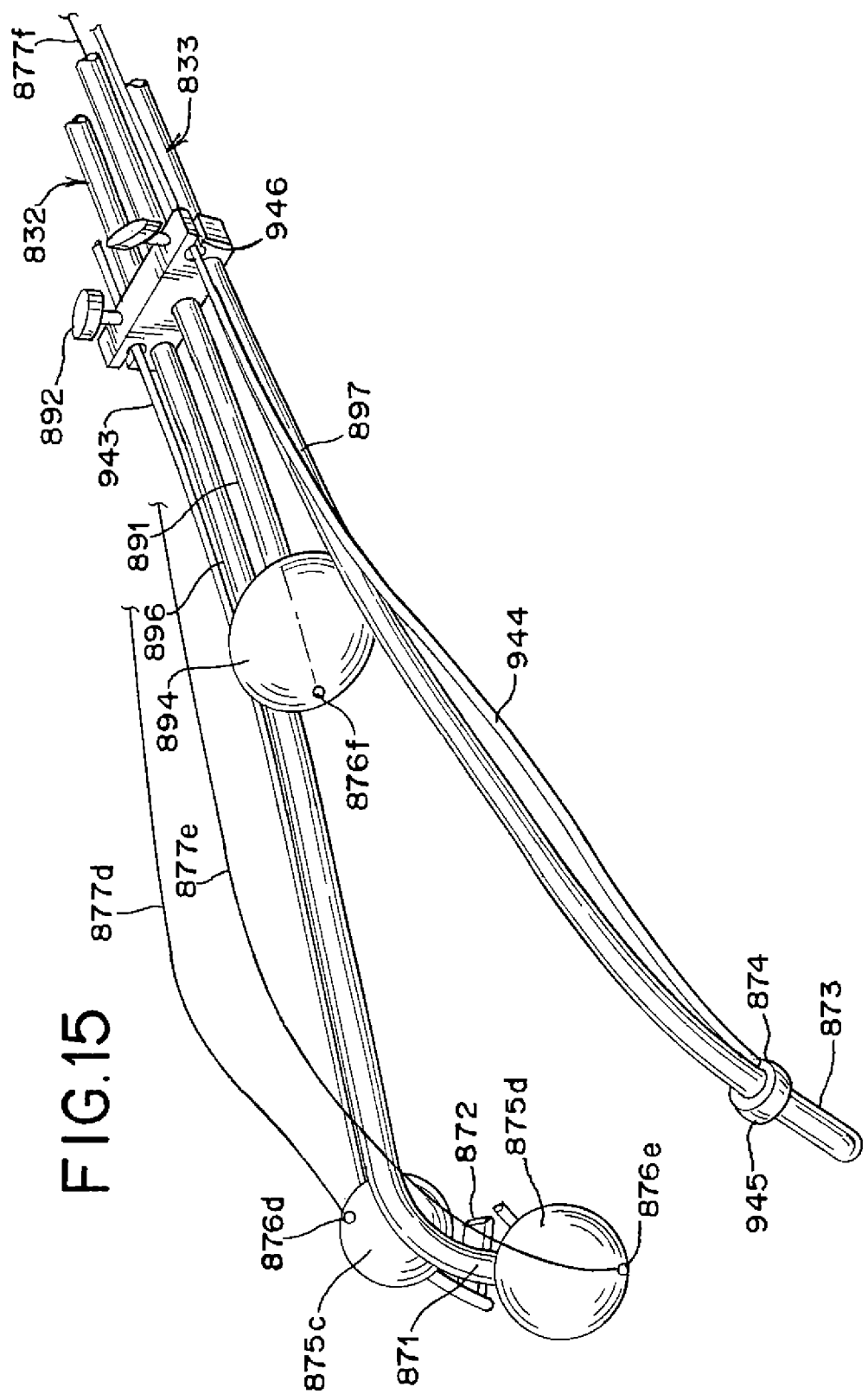
FIG. 15 is a perspective view of yet another embodiment of a brachytherapy system including a balloon component, illustrating dosing monitoring as well as a hyperthermia system.

FIG. 15 shows a colpostat system that incorporates a hyperthermia system by which heat can be applied to the cancerous area simultaneously with the radiation treatment or if desired in close association in time and location with the radiation treatment imparted by the colpostat means. More specifically, the hyperthermia system includes delivery tubes 943, 944 that extend between a target location and a hyperthermia fluid source (not shown) of generally known characteristics and structure, such hyperthermia fluid source being outside of the body. In this illustrative embodiment, each hyperthermia delivery tube 943, 944 is secured by the assembly unit 992. As shown, this securement can be achieved, for example, by having the tube pass through an opening 946 such as a slotted keyway through the assembly unit. In this illustration, such keyway opening is adjacent to the location at which the ovoid colpostat 932, 933 is secured by the assembly unit 992.

In this illustrative embodiment, the target location is in the vicinity of the location at which the colpostat delivers the radiation, which can be low dose radiation, for example. Thus, delivery tube 943 is positioned generally adjacent ovoid delivery location 971 of an ovoid such as colpostat 932. Hyperthermia delivery tube 944 is shown positioned in direct contact with a widened location 945 at the ovoid delivery location 873 in the other illustrated ovoid colpostat 933 illustrated in FIG. 15. Tube 944 applies heat in this colpostat area and generally adjacent to the radiation delivery site. If desired, the tube 944 can open into the widened location 945 to thereby provide flow of the hyperthermia treatment fluid into this location 945, whereby an integral hyperthermia treatment administration site is positioned at a specific location that is substantially at the radiation delivery site.

When all of the features and structures shown in FIG. 15 are implemented in a single system, the advantages of hyperthermia are combined with radiation treatment whereby the target tissue is raised in temperature during, or close in time before or after, radiation treatment, which can enhance the effectiveness of the radiation treatment. In addition, the detectors such as microdiodes or the like, as described elsewhere herein, provide "real time" in vivo detection and measurement of the radiation delivered, which can assist in tailoring a radiation regimen for the particular patient. Moreover, this detection and measurement is carried out at, or in very close proximity to the, location of the radiation treatment and, when desired, also of the hyperthermia treatment, with the objective of providing an unusually efficient and effective combination of patient treatment features.

FIG. 16 shows another colpostat, generally designated 833a, which has an internal distal delivery location 873 along the catheter-like body. Shielding element 874a and a second shielding element 875a, a balloon 875a, a detector 876, a transmission wire 877, and a conduit 876a are shown. The balloon 875a may be a radio therapeutic balloon that itself has at least one radio therapeutic member (not shown). Typically such a radio therapeutic member will be on a portion of this therapeutic balloon that is directed away from the tissue that is not to be subjected to radiation treatment by such a radio therapeutic member.

Figures 17, 18:
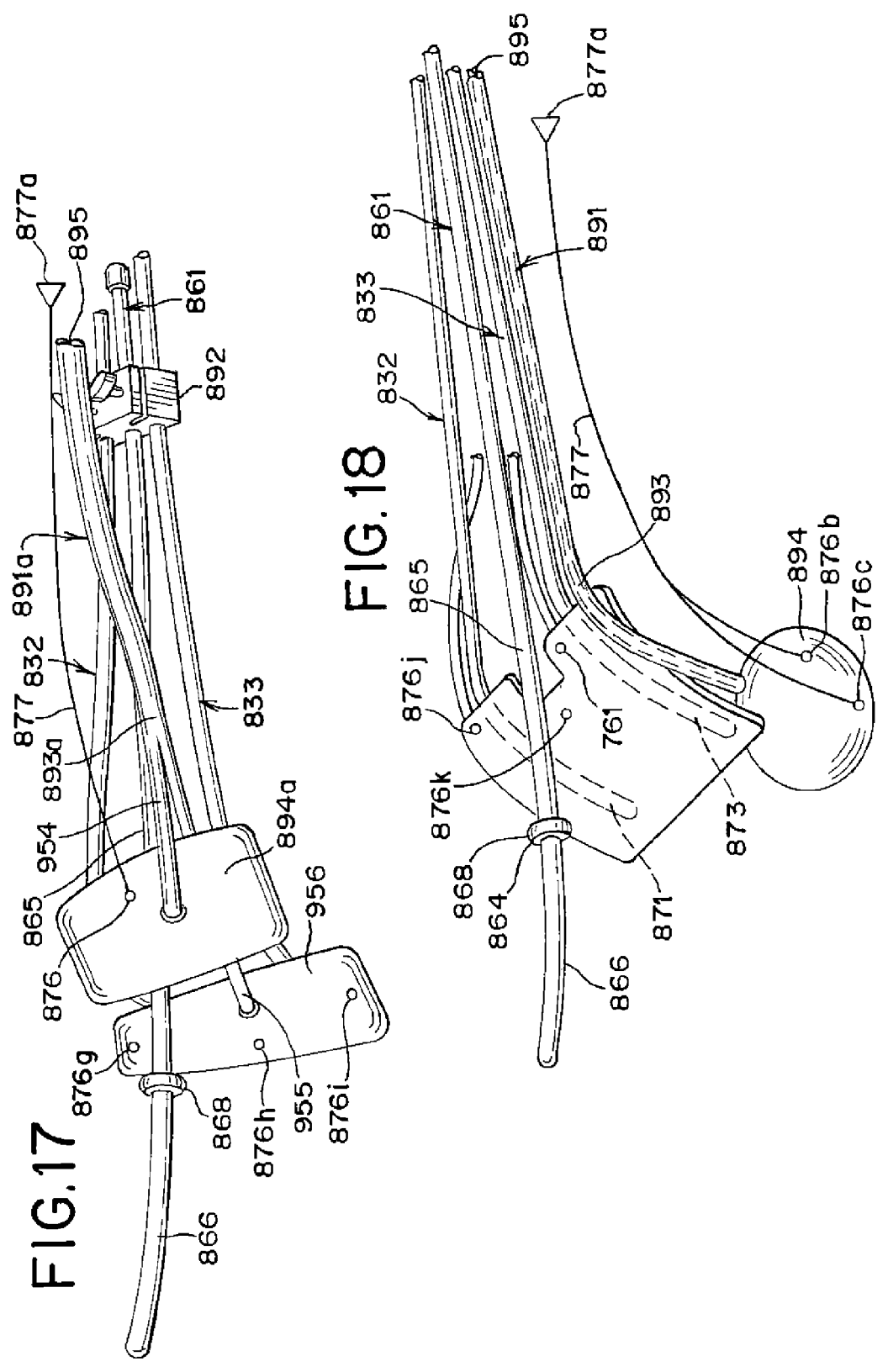

A first balloon, generally designated as 891a, is shown in FIG. 17 positioned so as to space colpostats (both ovoids here) away from the vaginal wall to assist in minimizing undesired radiation exposure. The illustrated balloon includes a shaft 893a shown as bifurcated into first branch 954 and a second branch 955. Branch 954 has an inflatable first wide-area balloon member 894a spaced therealong, while branch 955 has a second wide-area balloon member 956. The shaft 893a includes a lumen that is secured to a suitable device (not shown) of known construction and features that provide inflation fluid, typically saline liquid or gas such as air or nitrogen, into the lumen 895 and distally therethrough until exiting through an opening therein into the respective balloon members 894a and 956. In this illustrated arrangement, balloon 894a provides protection at the ovoid bends while balloon 956 provides protection at the distal colpostat delivery sites.

FIG. 17 is an embodiment of a colpostat assembly of the tandem and ovoid type for intrauterine treatment and with large surface area balloon members having one or more of the balloon features described herein. A first balloon, generally designated as 891a, is shown in FIG. 17 positioned so as to space both of the ovoids away from the vaginal wall to assist in minimizing undesired radiation exposure. The illustrated balloon includes a shaft 893a shown as bifurcated into first branch 954 and a second branch 955. Branch 954 has an inflatable first wide-area balloon member 894a spaced therealong, while branch 955 has a second wide-area balloon member 956. The shaft 893a includes a lumen that is secured to a suitable device (not shown) of known construction and features that provide inflation fluid, typically saline liquid or gas such as air or nitrogen, into the lumen 895 and distally therethrough until exiting through an opening therein into the respective balloon members 894a and 956. In this illustrated arrangement, balloon 894a provides protection at the ovoid bends while balloon 956 provided protection at the distal colpostat delivery sites.

Each branch 954, 955 can be independently operated by providing the lumen with dual longitudinal passageways, opening into the respective branches 954, 955. When desired, greater than two lumen passageways can be provided to selectively inflate and deflate respective multiple balloon members in this and other embodiments hereof.

The balloon or balloons of this or other embodiments may have radiopaque marking or may be radiopaque in whole or in part. Alternatively or additionally, the therapeutic balloons of the various embodiments include one or more detectors, such as microdiodes or diodes, attached or other devices or systems to provide "real-time" in vivo measuring of radiation. To this end a detector 876 is shown in FIG. 17. While transmission associated with a detector or detectors can be a wireless connection, lead or wire 877 is shown leading to data receptor 877a in FIG. 17 and FIG. 18. When any such balloons are therapeutic balloons, one or more radio therapeutic members, typically associated with at least one receiving member (not shown) when loading subsequent to initial colpostat catheter placement is to be practiced. In such situations, the radio therapeutic members will be remote from those locations of the therapeutic balloon that engage and otherwise protect tissue not to be treated from the radiation therapy provided by these therapeutic catheter types of devices.

In FIG. 18, two detectors 876b and 876c are shown on one of the balloon members. These detect radiation at different locations and can have a common lead (allowing for separate data paths) or separate leads to the data receptor. A detector or detectors can be included at 876g, 876h, 876i, 876j, 876k and 76I of FIGS. 17 and 18, each being shown as a wireless detector.

Several embodiments of colpostats and catheters with balloons or therapeutic balloons are shown herein. Each has a distal section or "leg" which typically includes the site at which the radiation emanates during treatment. In some embodiments, one or more of a balloon, a wide-surface balloon, a balloon that encompasses substantially an entire treatment portion of a colpostat or of multiple colpostats (such as ovoid pairs in FIG. 18), a shield, a detector, a hyperthermia delivery system are associated with or in some cases secured to the catheter body or colpostat, such as an ovoid distal section. With an embodiment or embodiments, this distal section is attachable and detachable to the rest of the colpostat. Structures and approaches such as those described herein including but not limited to attachment arrangements, detachable members, disposable members and so forth can be applied to or found in these types of devices.

FIG. 19 depicts a brachytherapy device for therapeutic radiation procedures that is capable of being inserted under the skin and through or around bodily tissue to the treatment site desired. Such can be at a surgical opening or surgical defect, and the device can be left in place for a desired treatment regimen and retrieved or removed when appropriate. This device includes a catheter 910 capable of performing functions as discussed herein. The distal end of this device has a probe 911 that facilitates insertion into the body, whether an existing body cavity or an opening made solely for the purpose of the brachytherapy procedure. The therapeutic balloon 920 is positioned along the device in this illustrated embodiment at a distal portion of the device. A plurality of treatment tubes or rods 950 are positioned generally along the catheter 910 and therapeutic balloon 920. As discussed herein with respect to other embodiments, the radio therapeutic rods or tubes 950 expand outwardly and generally radially in order to provide the treatment regimen to tissue areas generally along the therapeutic balloon 920. The extent of the outward movement of the balloon will depend upon the objectives of the brachytherapy procedure and the shape and size of the volume within the body within which the balloon is positioned during treatment.

One or more detectors 954 are included along the therapeutic balloon 920 or rods 950. One or more such detectors can be on the surface of the balloon, whether inside or outside surface, or be embedded within the balloon wall. Alternatively, one or more detectors can be secured to one or more of the radio therapeutic rods 950. The illustrated detectors are of the wireless variety as generally discussed herein. Typically these will be microdiodes and are instrumental in providing "real-time" in vivo measurement of radiation at the detector location.

This embodiment also incorporates a hyperthermia system by which heat can be applied to the cancerous area simultaneously with radiation time and location. In this particular embodiment, hyperthermia delivery tube 957 is directly associated with one or more of the radio therapeutic delivery tubes or rods 950. One embodiment shown in FIG. 19 has the hyperthermia delivery tube 957 attached to a radio therapeutic rod 950, and the distal portion 958 of the hyperthermia delivery system opens within the therapeutic balloon 920. The distal portion can project outside of the therapeutic balloon 950, projecting through a sealed opening of the balloon. Alternatively the hyperthermia delivery tube and its distal portion can remain outside of the therapeutic balloon. Typically, space saving can be realized with a dual lumen tube, one passageway of which is for radio therapeutic delivery, with the other passageway being for hyperthermia treatment delivery.

With devices such as illustrated in FIG. 19 or other devices and systems as discussed herein, electronic brachytherapy can be carried out with the device having a catheter type of body that is implanted within a cavity, such a lumpectomy cavity or an intrauterine cavity. In such systems, radiation is emitted only when the system is activated so that radiation is put into effect.

FIG. 20 depicts a balloon 960 of an elongated shape in cross-section. This embodiment includes other features included herein, with only the balloon being shown for simplicity. Same can be useful when the area in the body, such as a prostate, to be radiation treated is more easily reached by a non-circular balloon, such as a shape as illustrated. This type of balloon shape can be useful when it is important that the balloon be positioned to move or secure one body element, such as protecting the bladder during a prostate radiation treatment.

FIG. 20A depicts a balloon 961 that has a somewhat D-shaped cross-section. This provides a broad surface area 962 for either enhanced treatment surface area or enhanced area to engage and hold off healthy tissue from close positioning with respect to a body site being radiation treated.

Figure 21:
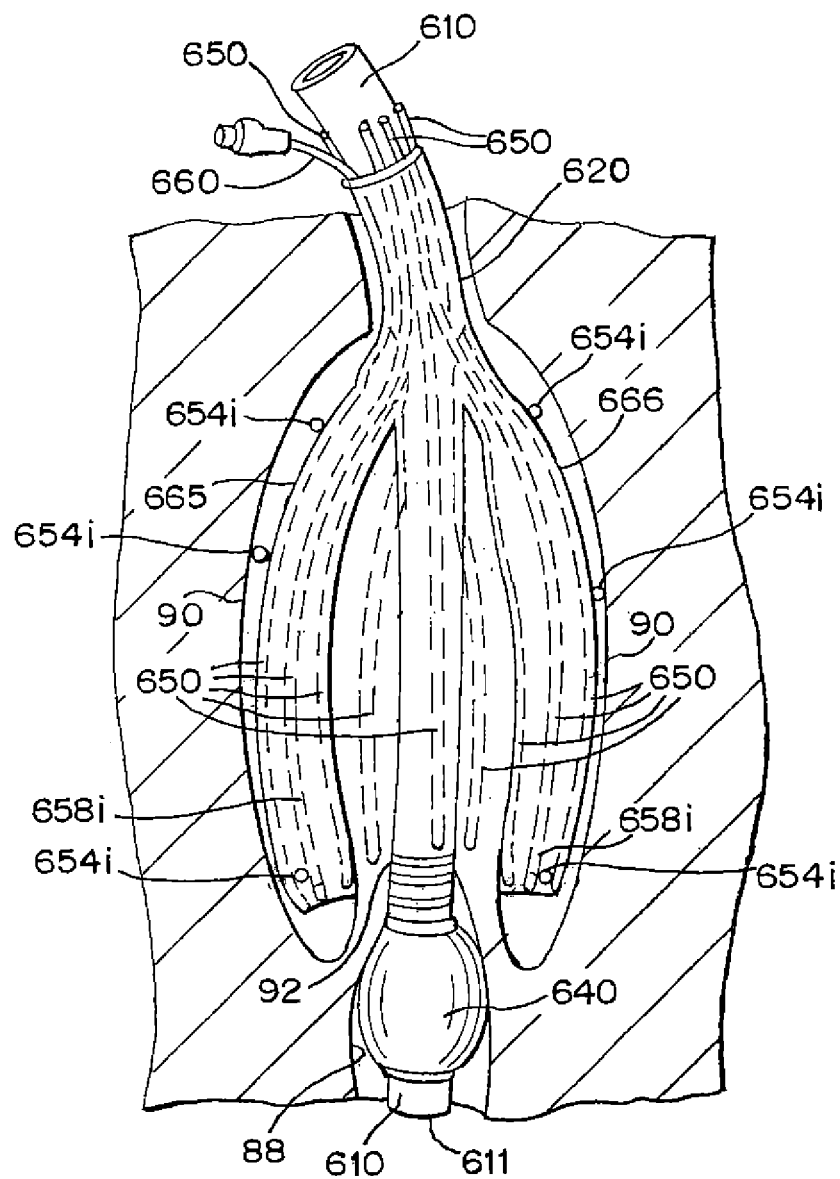
FIG. 21 is a generally schematic view that demonstrates another embodiment for use in the pyriform sinus area.

FIG. 21 has a general similarity to FIG. 11, and same can be for use in the hypopharynx. As in FIG. 11, this device includes a catheter 610, a secondary balloon 640, radio therapeutic tubes or rods 650, and an inflation tube 660. The therapeutic balloon 620 for this embodiment may be split at a generally proximal location into two chambers 665, 666 which inflate into each pyriform fossa. The radio therapeutic rods 650 typically are preloaded with radioactive members or materials and then positioned for movement with the balloon 620 such as by being slipped into rod receiving members of the therapeutic balloon. The therapeutic balloon is inserted into the hypopharynx 90. If needed the secondary balloon 640 can be inserted into the subglottic region. The therapeutic balloon 620 and secondary balloon 640 are inflated by means of one or two inflation tubes 660. A hole 611 and longitudinal passageway throughout the catheter 610 permit respiration during the course of the radiation therapy procedure. Multiple wireless detectors 654i are shown along the bifurcated therapeutic balloon 620, each also having positioned therewithin a hyperthermia delivery tube 657i having distal ends portions 658i.

Figure 22:
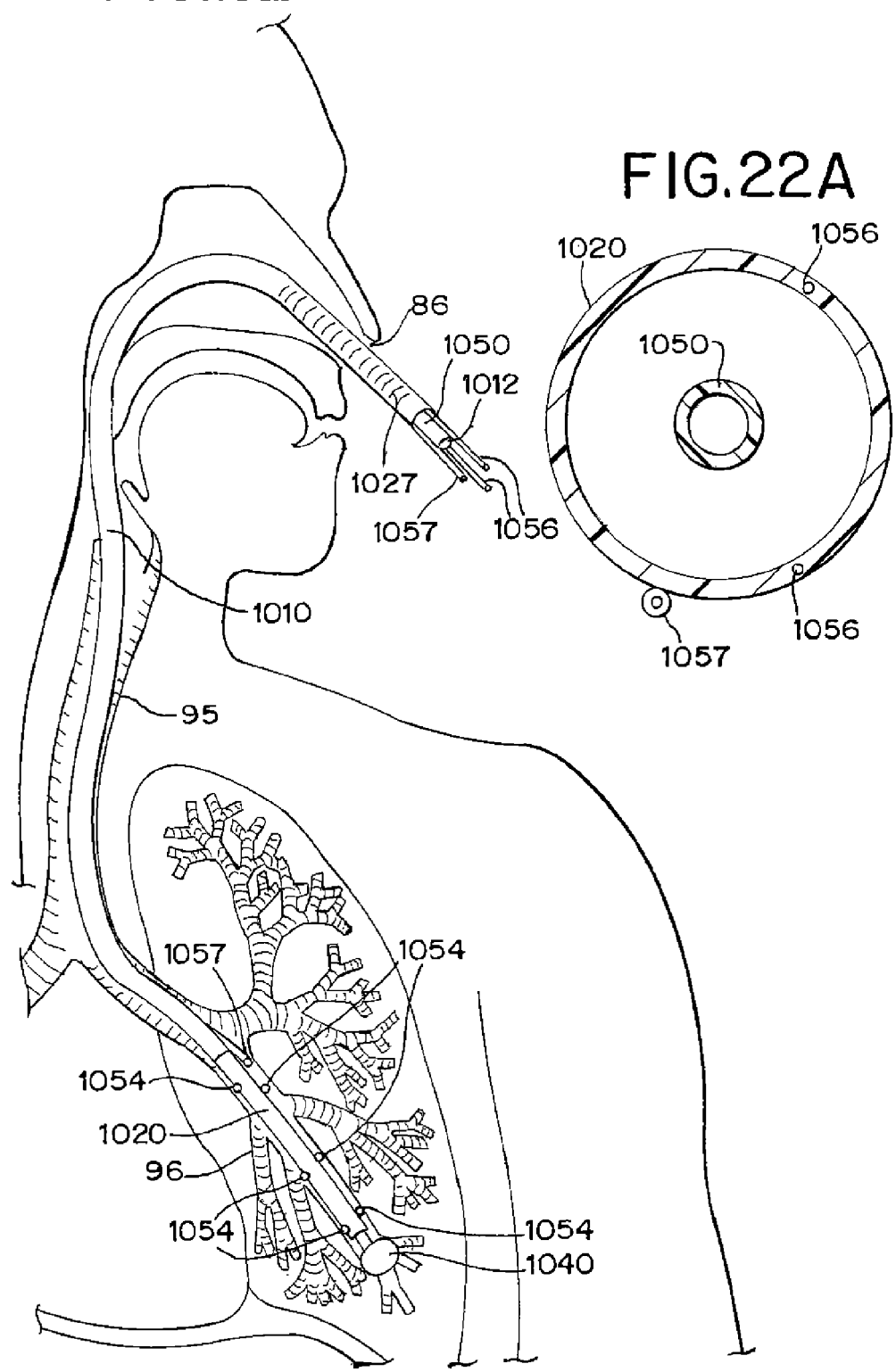
FIG. 22 is a generally schematic view illustrating another embodiment especially suitable for use in long bronchus.

FIG. 22 illustrates an embodiment for use of the system, device and method in the lung, particularly in the bronchus, whether upper or lower lobe, the lower lobe use being illustrated in this view. This illustrated embodiment includes an elongated catheter 1010, catheter lead 1012, therapeutic balloon 1020, radial therapeutic rods 1050 and an inflation tube (not shown). The radial therapeutic rods 1050 accommodate radioactive pellets or other radiation sources discussed herein. When provided, catheter 1012 guides the catheter into the mouth or the nose 86 and eventually into the lung trachea 95 and eventually into the bronchus 96. Once inserted into the prescribed location, the therapeutic balloon 1020 is inflated with a pressurized fluid source discussed elsewhere herein or as otherwise known. Multiple detectors 1054 are illustrated along the length of the therapeutic balloon. At least one hyperthermal tube 1057 is illustrated in this embodiment.

A secondary balloon 1040 is provided in this embodiment at the distal end or tip of the catheter in order to hold the catheter in place during treatment. A series of scale markings 1027 are shown along the proximal length of the catheter 1010 in order to allow the medical professional to mark the distance that the catheter, treatment balloon and secondary balloon are positioned within the lung. A typical catheter 1010 can have a length on the order of 40 cm and, for example, 36 cm thereof can be positioned internally of the patient during treatment. Transmission conduits 1056 can be provided for the detectors 1054. FIG. 22A is a somewhat schematic cross-sectional view that illustrates an embodiment of suitable relationships among the illustrated components for the lung bronchus treatment system.

FIG. 23 is similar to the embodiment of FIG. 22. Here, an alternative balloon 1031 is provided. This balloon 1031 can be receptive of radiopaque material to facilitate imaging and provide proper placement. Same also can function as a secondary balloon to stabilize positioning of the catheter. Balloon 1031 also can function, when loaded with radio therapeutic material, for treatment of lung sac area carcinoma. When access to the balloon 1031 is to be separate from access to the balloon 1020 (when provided), dual passageways 1067, 1068 are available, as generally shown in FIG. 23A.

As a general proposition, chemotherapy materials can be included in conjunction with one or more of the radiation treatment devices described herein. Such delivery can be, for example, practiced by way of delivery tubes such as those shown herein for a hyperthermia function in those instances where separate tubing is desired for chemotherapy delivery. Additionally or alternatively, one or more of the balloons or catheter in some embodiments can have impregnated into, infused onto, coated on, or otherwise carry chemotherapy materials separate and apart from being able to be delivered from the outside after insertion into the body. Chemicals or drugs along these lines can be provided in the form of microspheres or other organically bound or chemically bound substances as alternative chemotherapy or radioactive delivery systems. For example, delivery of Bacillum calmette-guerin (BCG) for bladder cancer treatment can be used. In other embodiments, the substance delivered by any of these means can be useful for pain maintenance, such as analgesic materials and pain or narcotic materials to provide pain relief during procedures, especially when the device protocol requires insertion within the body for extended time periods. These can include delayed release analgesics and the like.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A therapeutic catheter, comprising:
   a catheter body that is sized, shaped and adapted to not deform under pressure encountered during passage from an insertion location to a target location within a radiation treatment subject for radiation therapy at the target location, the catheter body having an outside surface;
   a therapeutic balloon associated with the catheter body, said therapeutic balloon having a collapsed condition and an expanded condition;
   one or more radio therapeutic sources having radioactivity, said therapeutic balloon being sized, shaped and adapted to position at least one of the radio therapeutic sources for radiation therapy when the balloon is inflated;
   at least one of the radio therapeutic sources comprises a plurality of elongated rods supporting radio therapeutic material and having an end portion longitudinally movable with respect to the catheter body to impart to at least one of the elongated rods movement between a first position and a second position at which the at least one of the elongated rods is bowed outwardly;
   wherein the plurality of elongated rods are secured together at respective distal end portions of each of the elongated rods and secured to a shaft, respective proximal end portions of at least two of the elongated rods are independently longitudinally movable and bow out in response to relative longitudinal movement between the distal end portions and the proximal end portions;
   at least one detector that collects data on radiation at a treatment location of the therapeutic catheter;
   a hyperthermia component that delivers hyperthermia treatment that interacts with radiation delivery by at least one of the radio therapeutic sources; and
   the data collected by the detector, wherein said data monitors interaction between at least one of the radio therapeutic sources and the hyperthermia component.

2. The therapeutic catheter in accordance with claim 1, wherein said detector is secured to the therapeutic balloon.

3. The therapeutic catheter in accordance with claim 1, further including a securement member affixed to the catheter, wherein the securement member is adapted to secure the therapeutic catheter to a radiation treatment subject, and the detector is associated with the securement member.

4. The therapeutic catheter in accordance with claim 3, wherein said securement member includes at least one anchoring catheter for insertion into a body orifice near the insertion location.

5. The therapeutic catheter in accordance with claim 1, further including a passageway longitudinally through the catheter body from a distal end to a proximal end of the catheter body, said passageway being large enough to accommodate excrement or other body fluid or gas flow therethrough during a radiation therapy procedure.

6. The therapeutic catheter in accordance with claim 1, wherein the therapeutic balloon is secured to a portion of the outside surface of the catheter body, and a receiving member for holding at least one of the radio therapeutic sources is outside of the therapeutic balloon.

7. The therapeutic catheter in accordance with claim 6, wherein said therapeutic balloon moves at least one of the radio therapeutic sources to the target location and provides manipulation of the target location within the radiation treatment subject by engagement between the therapeutic balloon and the target location upon inflation of the therapeutic balloon.

8. The therapeutic catheter in accordance with claim 1, wherein the catheter is a colpostat having a distal end portion treatment location, and said therapeutic balloon substantially fully incorporates the distal end portion treatment location of the colpostat.

9. The therapeutic catheter in accordance with claim 8, including at least two colpostats secured to the catheter, and the therapeutic balloon substantially fully incorporates the distal end portion of each said colpostat.

10. The therapeutic catheter in accordance with claim 1, wherein the therapeutic balloon has a surface wall and a receiving member elongated pocket is positioned on the surface wall of the therapeutic balloon.

11. The therapeutic catheter in accordance with claim 1, further including a receiving member, the receiving member being a loop of material which substantially affixes at least one of the radio therapeutic sources along a contour of the therapeutic balloon, and the loop of material substantially affixes one of the elongated rods along the contour of the therapeutic balloon.

12. The therapeutic catheter in accordance with claim 1, wherein the therapeutic balloon is substantially longer than wide and is sized, shaped and adapted such that when inflated the therapeutic balloon engages internal tissue of a region of an internal live body cavity, the catheter body having a longitudinal passageway that is adapted to extend from outside the live body cavity to an area of the therapeutic balloon said passageway permitting flow of nutrients therethrough during radio therapy.

13. A therapeutic catheter in accordance with claim 1, wherein chemotherapy materials, analgesic materials, or a combination thereof is delivered by a tube that is impregnated, infused, coated or carried by the therapeutic balloon, wherein said materials are in the form of fluids, microspheres, organically bound substances, chemically bound substances, or combinations thereof.

14. The therapeutic catheter in accordance with claim 1, wherein the hyperthermia component is of an energy type selected from the group consisting of thermal, microwave, ultrasonic, radiant and combinations thereof, which energy is applied without or with radiation, and whether simultaneously, pre-irradiation or post-irradiation.

15. A therapeutic catheter, comprising:
a catheter body that is sized, shaped and adapted to not deform under pressure encountered during passage from an insertion location to a target location within a radiation treatment subject for radiation therapy at the target location, the catheter body having an outside surface;
a therapeutic balloon associated with the catheter body, said therapeutic balloon having a collapsed condition and an expanded condition;
one or more radio therapeutic sources having radioactivity, said therapeutic balloon being sized, shaped and adapted to position at least one of the radio therapeutic sources for radiation therapy when the balloon is inflated;
at least one of the radio therapeutic sources comprises a plurality of elongated rods supporting radio therapeutic material and having an end portion longitudinally movable with respect to the catheter body to impart to at least one of the plurality of elongated rods movement between a first position and a second position at which the at least one of the elongated rods is bowed outwardly;
wherein the plurality of elongated rods are secured together at respective distal end portions of the plurality of elongated rods and secured to a shaft, the elongated rods being secured together at respective proximal end portions of the plurality of elongated rods that are longitudinally movable with respect to the shaft and bow outwardly in response to relative longitudinal movement between the distal end portions and proximal end portions;
at least one detector that collects data on radiation at a treatment location of the therapeutic catheter;
a hyperthermia component that delivers hyperthermia treatment that interacts with radiation delivery by at least one of the radio therapeutic sources; and
the data collected by the detector, wherein said data monitors interaction between at least one of the radio therapeutic sources and the hyperthermia component.

16. A therapeutic catheter in accordance with claim 15, wherein chemotherapy materials, analgesic materials, or a combination thereof is delivered by a tube that is impregnated, infused, coated or carried by the therapeutic balloon, wherein said materials are in the form of fluids, microspheres, organically bound substances, chemically bound substances, or combinations thereof.

17. The therapeutic catheter in accordance with claim 15, wherein the hyperthermia component is of an energy type selected from the group consisting of thermal, microwave, ultrasonic, radiant and combinations thereof, which energy is applied without or with radiation, and whether simultaneously, pre-irradiation or post-irradiation.

18. The therapeutic catheter in accordance with claim 15, wherein the therapeutic balloon is secured to a portion of the outside surface of the catheter body, and a receiving member for holding at least one of the radio therapeutic sources is outside of the therapeutic balloon.

19. The therapeutic catheter in accordance with claim 15, wherein the catheter is a colpostat having a distal end portion treatment location, and said therapeutic balloon substantially fully incorporates the distal end portion treatment location of the colpostat.

20. The therapeutic catheter in accordance with claim 15, wherein the therapeutic balloon has a surface wall and a receiving member elongated pocket is positioned on the surface wall of the therapeutic balloon.

21. The therapeutic catheter in accordance with claim 15, further including a receiving member, the receiving member being a loop of material which substantially affixes at least one of the radio therapeutic sources along a contour of the therapeutic balloon, and the loop of material substantially affixes one of the elongated rods along the contour of the therapeutic balloon.

22. The therapeutic catheter in accordance with claim 15, wherein the therapeutic balloon is substantially longer than wide and is sized, shaped and adapted such that when inflated the therapeutic balloon engages internal tissue of a region of an internal live body cavity, the catheter body having a longitudinal passageway from outside the live body cavity to an area of the therapeutic balloon, said passageway permitting flow of nutrients therethrough during radio therapy.

23. The therapeutic catheter in accordance with claim 15, wherein said detector is secured to the therapeutic balloon.

24. The therapeutic catheter in accordance with claim 15, further including a securement member affixed to the catheter, wherein the securement member secures the therapeutic catheter to the radiation treatment subject.

25. The therapeutic catheter in accordance with claim 15, wherein the catheter body and the therapeutic balloon include respective distal ends, and said distal end of the catheter body extends distally of said distal end of the therapeutic balloon, further including a passageway longitudinally through the catheter body from said distal end of the catheter body to said proximal end of the catheter body, said passageway being large enough to accommodate excrement or other body fluid or gas flow therethrough during a radiation therapy procedure.

26. The therapeutic catheter in accordance with claim 15, wherein the therapeutic balloon is secured to a portion of the outside surface of the catheter body.

27. The therapeutic catheter in accordance with claim 15, wherein said therapeutic balloon provides manipulation of the target location within the radiation treatment subject by engagement between the therapeutic balloon and the target location upon inflation of the therapeutic balloon.

28. A therapeutic catheter, comprising:
a catheter body that is sized, shaped and adapted to not deform under pressure encountered during passage from an insertion location to a target location within a radiation treatment subject for radiation therapy at the target location, the catheter body having an outside surface;
a therapeutic balloon associated with the catheter body, said therapeutic balloon having a collapsed condition and an expanded condition;
one or more radio therapeutic sources having radioactivity, said therapeutic balloon being sized, shaped and adapted to position at least one of the radio therapeutic sources for radiation therapy when the balloon is inflated;
wherein the catheter includes scale markings along a proximal portion thereof, and a secondary balloon along the catheter near a distal end portion thereof expands after insertion into a lung bronchus, wherein the scale markings and secondary balloon cooperate for reproducible placement of the therapeutic balloon with respect to a lung carcinoma;
at least one detector that collects data on radiation at a treatment location of the therapeutic catheter;
a hyperthermia component that delivers hyperthermia treatment that interacts with radiation delivery by at least one of the radio therapeutic sources; and
the data collected by the detector, wherein said data monitors interaction between at least one of the radio therapeutic sources and the hyperthermia component.

29. A therapeutic catheter in accordance with claim 28, wherein chemotherapy materials, analgesic materials, or a combination thereof is delivered by a tube that is impregnated, infused, coated or carried by the therapeutic balloon, wherein said materials are in the form of fluids, microspheres, organically bound substances, chemically bound substances, or combinations thereof.

30. The therapeutic catheter in accordance with claim 28, wherein the hyperthermia component is of an energy type selected from the group consisting of thermal, microwave, ultrasonic, radiant and combinations thereof, which energy is applied without or with radiation, and whether simultaneously, pre-irradiation or post-irradiation.

31. The therapeutic catheter in accordance with claim 28, wherein the catheter is a colpostat having a distal end portion treatment location, and said therapeutic balloon substantially fully incorporates the distal end portion treatment location of the colpostat.

32. The therapeutic catheter in accordance with claim 28, including at least two colpostats secured to the catheter, and the therapeutic balloon substantially fully incorporates a distal end portion of each said colpostat.

33. The therapeutic catheter in accordance with claim 28, wherein the therapeutic balloon has a surface wall and a receiving member elongated pocket is positioned on the surface wall of the therapeutic balloon.

34. The therapeutic catheter in accordance with claim 28, wherein the therapeutic balloon is substantially longer than wide and is sized, shaped and adapted such that when inflated the therapeutic balloon engages internal tissue of a region of an internal live body cavity, the catheter body having a longitudinal passageway from outside the live body cavity to an area of the therapeutic balloon, said passageway permitting flow of nutrients therethrough during radio therapy.

* * * * *